United States Patent
Etzioni et al.

(10) Patent No.: US 11,763,915 B2
(45) Date of Patent: Sep. 19, 2023

(54) METHODS FOR DETECTING NUCLEIC ACID VARIANTS

(71) Applicant: Ultima Genomics, Inc., Newark, CA (US)

(72) Inventors: Yoav Etzioni, Tel Aviv (IL); Simchon Faigler, Bet Izhak (IL); Gilad Almogy, Palo Alto, CA (US); Mark Pratt, Bozeman, MT (US); Florian Oberstrass, Menlo Park, CA (US)

(73) Assignee: Ultima Genomics, Inc., Newark, CA (US)

( * ) Notice: Subject to any disclaimer, the term of this patent is extended or adjusted under 35 U.S.C. 154(b) by 478 days.

(21) Appl. No.: 16/864,981

(22) Filed: May 1, 2020

(65) Prior Publication Data

US 2020/0372971 A1    Nov. 26, 2020

Related U.S. Application Data

(60) Provisional application No. 62/971,530, filed on Feb. 7, 2020, provisional application No. 62/842,534, filed on May 3, 2019.

(51) Int. Cl.
| | | |
|---|---|---|
| *G16B 20/20* | (2019.01) | |
| *C12Q 1/6874* | (2018.01) | |
| *G16B 30/10* | (2019.01) | |
| *G06F 17/00* | (2019.01) | |
| *G16B 20/00* | (2019.01) | |
| *G16B 30/00* | (2019.01) | |
| *G01N 21/64* | (2006.01) | |

(52) U.S. Cl.
CPC ........... *G16B 20/20* (2019.02); *C12Q 1/6874* (2013.01); *G06F 17/00* (2013.01); *G16B 20/00* (2019.02); *G16B 30/00* (2019.02); *G16B 30/10* (2019.02); *C12Q 2600/156* (2013.01); *C12Q 2600/158* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 8,772,473 B2 | 7/2014 | Huang | |
| 9,416,413 B2 * | 8/2016 | Schultz | ................ C12Q 1/6869 |
| 9,817,944 B2 | 11/2017 | Kural | |
| 10,344,328 B2 | 7/2019 | Barbee | |
| 11,220,709 B2 | 1/2022 | Oberstrass et al. | |
| 11,220,710 B2 | 1/2022 | Oberstrass et al. | |
| 2011/0270533 A1 | 11/2011 | Zhang | |
| 2013/0073214 A1 * | 3/2013 | Hyland | ................ G16B 30/00 |
| | | | 702/19 |
| 2013/0090860 A1 | 4/2013 | Sikora | |
| 2014/0052381 A1 | 2/2014 | Utiramerur | |
| 2015/0066824 A1 | 3/2015 | Harris | |
| 2016/0078094 A1 * | 3/2016 | Popescu | ................ G16B 40/00 |
| | | | 707/722 |
| 2017/0335387 A1 | 11/2017 | Brinza | |
| 2018/0330051 A1 | 11/2018 | Hubbell | |
| 2020/0372971 A1 | 11/2020 | Etzioni | |
| 2020/0377937 A1 | 12/2020 | Pratt | |
| 2020/0392584 A1 | 12/2020 | Almogy | |
| 2021/0010075 A1 | 1/2021 | Oberstrass | |
| 2021/0054442 A1 | 2/2021 | Pratt et al. | |
| 2021/0147930 A1 | 5/2021 | Oberstrass et al. | |
| 2021/0147931 A1 | 5/2021 | Oberstrass et al. | |
| 2022/0170089 A1 | 6/2022 | Pratt et al. | |
| 2023/0060685 A1 | 3/2023 | Pratt et al. | |

FOREIGN PATENT DOCUMENTS

| | | |
|---|---|---|
| WO | 2019084158 A1 | 5/2019 |
| WO | 2020227137 A1 | 11/2020 |
| WO | 2020227143 A1 | 11/2020 |
| WO | 2020236630 A1 | 11/2020 |
| WO | 2021007495 A1 | 1/2021 |
| WO | 2022099270 A1 | 5/2022 |
| WO | 2022099271 A1 | 5/2022 |
| WO | 2022109574 A1 | 5/2022 |

OTHER PUBLICATIONS

Kristof De Beuf, Joachim De Schrijver, Olivier Thas, Wim Van Criekinge, Rafael A Irizarry and Lieven Clement. Improved basecalling and quality scores for 454 sequencing based on a Hurdle Poisson model. BMC Bioinformatics 3:303 (Year: 2012).*

Depristo, M.A. et al. (May 2011, e-pub. Apr. 10, 2011). "A Framework for Variation Discovery and Genotyping Using Next-Generation DNA Sequencing Data," Nature Genetics 43(5):491-498.

Hwang, S. et al. (Dec. 7, 2015). "Systematic Comparison of Variant Calling Pipelines Using Gold Standard Personal Exome Variants," Scientific Reports 5(17875):1-8.

(Continued)

*Primary Examiner* — G. Steven Vanni
*Assistant Examiner* — Robert James Kallal
(74) *Attorney, Agent, or Firm* — MORRISON & FOERSTER LLP

(57) ABSTRACT

Methods for detecting a short genetic variant in a test sample are described herein. In some exemplary methods, the short genetic variant is called using one or more match scores, which are determined using one or more sequencing data sets obtained from a test nucleic acid molecule, wherein the test sequencing data sets are determined by sequencing the test nucleic acid molecule using non-terminating nucleotides provided in separate nucleotide flows according to a flow-cycle order. Also described herein are methods of sequencing a test nucleic acid molecule using two or more different flow-cycle orders and/or extended flow cycle orders having five or more nucleotide flows per flow cycle.

19 Claims, 11 Drawing Sheets

Specification includes a Sequence Listing.

(56) References Cited

OTHER PUBLICATIONS

Poplin, R. et al. (Jul. 24, 2018). "Scaling Accurate Genetic Variant Discovery to Tens of Thousands of Samples," BioRxiv, located at https://www.biorxiv.org/content/biorxiv/early/2017/11/14/201178.1.full.pdf, last visited on Aug. 7, 2020, 22 pages.
U.S. Appl. No. 16/864,971, filed May 1, 2020 by Mark Pratt et al. (Copy not submitted herewith pursuant to the waiver of 37 C.F.R. §1.98(a)(2)(iii) issued by the Office dated Sep. 21, 2004).
U.S. Appl. No. 16/875,645, filed May 15, 2020 by Gilad Almogy et al. (Copy not submitted herewith pursuant to the waiver of 37 C.F.R. §1.98(a)(2)(iii) issued by the Office dated Sep. 21, 2004).
Zook, J. M. et al. (Apr. 1, 2019). "An Open Resource for Accurately Benchmarking Small Variant and Reference Calls," Nature Biotechnology 37:561-566, 13 pages.
International Preliminary Report on Patentability, dated Nov. 2, 2021, for PCT Application No. PCT/US2020/031147, filed May 1, 2020, 9 pages.
International Search Report and Written Opinion, dated Aug. 12, 2020, for PCT Application No. PCT/US2020/031147, filed May 1, 2020, 18 pages.
U.S. Appl. No. 18/076,214, filed Dec. 6, 2022, Oberstrass et al. (Copy not submitted herewith pursuant to the waiver of 37 C.F.R. §1.98(a)(2)(iii) issued by the Office dated Sep. 21, 2004).

* cited by examiner

TATGGTCGTCGA        R1
 TGGTCGTCGAGC       R2
TATATGGTCGTC        R3
────────────────────────
TATATGGTCATCGAGCTAT H1
TATATGGTCGTCGAGCTAT H2

FIG. 2A

R1 Sequencing Data Set

| Base Count | Cycle 1 | | | | Cycle 2 | | | | Cycle 3 | | | | Cycle 4 | | | | Cycle 5 | | | |
| | 1 T | 2 A | 3 C | 4 G | 5 T | 6 A | 7 C | 8 G | 9 T | 10 A | 11 C | 12 G | 13 T | 14 A | 15 C | 16 G | 17 T | 18 A | 19 C | 20 G |
|---|---|---|---|---|---|---|---|---|---|---|---|---|---|---|---|---|---|---|---|---|
| 0 | 0.0010 ○ | 0.0010 ○ | 0.9988 ○ | 0.9988 ○ | 0.0010 ○ | 0.9988 ○ | 0.9988 ○ | 0.0001 | 0.0010 ○ | 0.9988 ○ | 0.0010 ○ | 0.0010 ○ | 0.0010 ○ | 0.9988 ○ | 0.0010 ○ | 0.0010 ○ | 0.9988 ○ | 0.0010 ○ | 0.9988 ○ | 0.9988 ○ |
| 1 | 0.9979 ● | 0.9979 ● | 0.0010 | 0.0010 | 0.9979 ● | 0.0010 | 0.0010 | 0.9979 ● | 0.9979 ● | 0.0010 | 0.9979 ● | 0.9979 ● | 0.9979 ● | 0.0010 | 0.9979 ● | 0.9979 ● | 0.0010 | 0.9979 ● | 0.0010 | 0.0010 |
| 2 | 0.0010 ○ | 0.0010 | 0.0001 | 0.0001 | 0.0010 | 0.0001 | 0.0001 | 0.0010 ○ | 0.0010 | 0.0001 | 0.0010 ○ | 0.0010 ○ | 0.0010 ○ | 0.0001 | 0.0010 ○ | 0.0010 ○ | 0.0001 | 0.0010 ○ | 0.0001 | 0.0001 |
| 3 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 | 0.0001 |

| Base Count | Cycle 1 | | | | | Cycle 2 | | | | | Cycle 3 | | | | | Cycle 4 | | | | | Cycle 5 | | | | |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| | T | A | C | G | T | A | C | G | T | A | C | G | T | A | C | G | T | A | C | G |
| 0 | 0.0010 | 0.0010 | 0.9988 | 0.9988 | 0.0010 | 0.9988 | 0.9988 | 0.0001 | 0.0010 | 0.9988 | 0.0010 | 0.0010 | 0.9988 | 0.0010 | 0.9988 | 0.9988 | 0.0010 | 0.9988 | 0.0010 | 0.0010 |
| 1 | 0.9979 | 0.9979 | 0.0010 | 0.0010 | 0.9979 | 0.0010 | 0.0010 | 0.0010 | 0.9979 | 0.0010 | 0.9979 | 0.9979 | 0.0010 | 0.9979 | 0.0010 | 0.0010 | 0.9979 | 0.0010 | 0.9979 | 0.9979 |
| 2 | 0.0010 | 0.0010 | 0.0001 | 0.0001 | 0.0010 | 0.0001 | 0.0001 | 0.9979 | 0.0010 | 0.0001 | 0.0010 | 0.0010 | 0.0001 | 0.0010 | 0.0001 | 0.0001 | 0.0010 | 0.0001 | 0.0010 | 0.0010 |
| 3 | 0.0001 | 0.0001 | 0.0001 | 0.0001 | 0.0001 | 0.0001 | 0.0001 | 0.0010 | 0.0001 | 0.0001 | 0.0001 | 0.0001 | 0.0001 | 0.0001 | 0.0001 | 0.0001 | 0.0001 | 0.0001 | 0.0001 | 0.0001 |

FIG. 8

SEQUENCE LISTING

```
<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1
tatggtcgtc ga                                                        12

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct

<400> SEQUENCE: 2
tatggtcatc ga                                                        12

<210> SEQ ID NO 3
<211> LENGTH: 12
<212> TYPE: DNA
<213> ORGANISM: Artificial Sequence
<220> FEATURE:
<223> OTHER INFORMATION: Synthetic Construct

<400> SEQUENCE: 3
tggtcgtcga gc                                                        12

<210> SEQ ID NO 4
<211> LENGTH: 12
<212> TYPE: DNA
<213> ORGANISM: Artificial Sequence
<220> FEATURE:
<223> OTHER INFORMATION: Synthetic Construct

<400> SEQUENCE: 4
tatatggtcg tc                                                        12

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
tatatggtca tcgagctat                                                 19

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
tatatggtcg tcgagctat                                                 19

<210> SEQ ID NO 7
<211> LENGTH: 12
<212> TYPE: DNA
<213> ORGANISM: Artificial Sequence
```

```
<220> FEATURE:
<223> OTHER INFORMATION: Synthetic Construct

<400> SEQUENCE: 7
tatggtcgtc ga                                                            12

<210> SEQ ID NO 8
<211> LENGTH: 12
<212> TYPE: DNA
<213> ORGANISM: Artificial Sequence
<220> FEATURE:
<223> OTHER INFORMATION: Synthetic Construct

<400> SEQUENCE: 8
tatggtcgat cg                                                            12
```

METHODS FOR DETECTING NUCLEIC ACID VARIANTS

CROSS-REFERENCE TO RELATED APPLICATIONS

This application claims the priority benefit of U.S. Provisional Patent Application Ser. No. 62/842,534, filed May 3, 2019; and U.S. Provisional Patent Application Ser. No. 62/971,530, filed Feb. 7, 2020; the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165272000540SEQLIST.TXT, date recorded: Apr. 27, 2020, size: 5 KB).

FIELD OF THE INVENTION

Described herein are methods of sequencing a polynucleotide, including methods for generating and/or analyzing sequencing data, including the detection of genetic variants.

BACKGROUND

Genetic variants in a DNA sample can be detected by sequencing the DNA in the sample, aligning the sequence to a references sequence and evaluating differences. High confidence differences between the sequenced DNA and the reference sequence are called as variants for the organism from which the DNA sample is derived. Next-generation sequencing has provided researches and clinical laboratories the tools needed to simultaneously sequence many different nucleic acid molecules in a single sample, generating significant amounts of data to analyze.

Additionally, reversible-terminator sequencing-by-synthesis (for example, reversibly terminated, dye-labeled sequencing methods) provide a single differentiated signal for each base, and therefore single-signal sequencing errors can result in erroneous variant calls. In some cases, this may be overcome by high depth sequencing, effectively overwhelming the erroneous calls with a true positive signal, but sequencing at such a high depth is expensive and time consuming.

A need for highly-efficient and accurate base calling and variant calling protocols remain needed in the art.

BRIEF SUMMARY OF THE INVENTION

Described herein are methods for detecting short genetic variant in a test sample containing nucleic acid molecules, which may be, in certain embodiments, computer-implemented methods. Also described herein are systems for carrying out such methods. Further described are methods of sequencing nucleic acid molecules.

In some embodiments, a method for detecting a short genetic variant in a test sample comprises (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample.

In some embodiments of the above method, the step of obtaining comprises sequencing the test nucleic acid molecule using non-terminating nucleotides provided in separate nucleotide flows according to the flow-cycle order.

In some embodiments of the above method, the target short genetic variant is pre-selected prior to calling the presence or absence of the target short genetic variant in the test sample. In some embodiments, the target short genetic variant is selected after calling the presence or absence of the target short genetic variant in the test sample based on a confidence of the call. In some embodiments, the method further comprises generating a personalized biomarker panel for a subject associated with the test sample, the biomarker panel comprising the target short genetic variant.

In some embodiments of the above method, the method further comprises selecting the flow-cycle order.

In some embodiments, the target sequencing data set is an expected target sequencing data set or the reference sequencing data set is an expected reference sequencing data set. In some embodiments, the expected target sequencing data set and the expected reference sequencing data set are obtained by sequencing the target sequence and the reference sequence in silico.

In some embodiments of the above method, the target sequencing data set differs from the reference sequencing data at more than two non-consecutive flow positions. In some embodiments, the target sequencing data set differs from the reference sequencing data at more than two consecutive flow positions. In some embodiments, the target sequence differs from the reference sequence at X base positions, and wherein the target sequencing data set differs from the reference sequencing data at (X+2) or more consecutive flow positions. In some embodiments, the (X+2) flow position differences comprise differences between values substantially equal to zero and values substantially greater than zero. In some embodiments, the target sequencing data set differs from the reference sequencing data set across one or more flow-cycles. In some embodiments, the flow signals comprise a base count indicative of a number of bases of the test nucleic acid molecule sequenced at each flow position.

In some embodiments of the above method, the flow signals comprise a statistical parameter indicative of a likelihood for at least one base count at each flow position, wherein the base count is indicative of a number of bases of the test nucleic acid molecule sequenced at the flow position. In some embodiments, the flow signals comprise a statistical parameter indicative of a likelihood for a plurality of base counts at each flow position, wherein each base count is indicative of a number of bases of the test nucleic acid molecule sequenced at the flow position.

In some embodiments of the above method, step (c) comprises (i) selecting the statistical parameter at each flow position in the test sequencing data set that corresponds with a base count of the target sequence at that flow position, and determining the match score indicative of the likelihood that the test sequencing data set matches the target sequence; or (ii) selecting the statistical parameter at each flow position in the test sequencing data set that corresponds with a base count of the reference sequence at that flow position, and determining the match score indicative of the likelihood that the test sequencing data set matches the reference sequence. In some embodiments, the match score determined in step (c) is a combined value of the selected statistical parameters across the flow positions in the test sequencing data set. In some embodiments, step (c) comprises determining the match score indicative of the likelihood that the test sequencing data set matches the target sequence. In some embodiments, step (c) comprises determining the match score indicative of the likelihood that the test sequencing data set matches the reference sequence.

In some embodiments of the above method, the one or more test sequencing data sets comprises a plurality of test sequencing data sets. In some embodiments, the presence or absence of the target short genetic variant is separately called for each of the one or more test sequencing data sets. In some embodiments, at least a portion of the plurality of test sequencing data sets are associated with different test nucleic acid molecules have different sequencing start positions.

In some embodiments of the above method, the flow-cycle order comprises 4 separate flows repeated in the same order. In some embodiments, the flow-cycle order comprises 5 or more separate flows.

In some embodiments of the above method, the method is a computer-implemented method. For example, in some embodiments, the computer-implemented method comprises selecting the target short genetic variant using one or more processors; obtaining the one or more test sequencing data sets by receiving, at the one or more processors, the one or more test sequencing data sets; determining the one or more match scores using the one or more processors; and calling the presence or absence of the target short genetic variant in the test sample using the one or more processors.

Also provided herein is a system, comprising: one or more processors; and a non-transitory computer-readable medium that stores one or more programs comprising instructions for implementing the above methods.

In some embodiments, a method for detecting a short genetic variant in a test sample comprises (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

In some embodiments of the above method, the method comprises sequencing the test nucleic acid molecules using non-terminating nucleotides provided in separate nucleotide flows according to the first flow-cycle order, and sequencing the test nucleic acid molecules using non-terminating nucleotides provided in separate nucleotide flows according to the second flow-cycle order.

In some embodiments of the above method, the match score is indicative of a likelihood that the first test sequencing data set matches the candidate sequence, or the likelihood that the second test sequencing data set matches the candidate sequence. In some embodiments, the match score is indicative of a likelihood that both the first test sequencing data set and the second sequencing data set match the candidate sequence.

In some embodiments of the above method, the one or more candidate sequences comprises two or more different candidate sequences, the method comprising, for each nucleic acid molecule associated with a first sequencing data set and a second sequencing data set: selecting a candidate sequence from the two or more different candidate sequences, wherein the selected candidate sequence has the highest likelihood match with the first test sequencing data set, the second test sequencing data set, or both; and calling, using the selected candidate sequence, the presence or absence of the short genetic variant in the test sample. In some embodiments, at least one non-selected candidate sequence from the two or more different candidate sequences differs from the selected candidate sequence at two or more flow positions according to the first flow-cycle order or the second flow-cycle order. In some embodiments, at least one non-selected candidate sequence from the two or more different candidate sequences differs from the selected candidate sequence at two or more flow positions according to both the first flow-cycle order and the second flow-cycle order. In some embodiments, at least one non-selected candidate sequence from the two or more different candidate sequences differs from the selected candidate sequence at two or more non-consecutive flow positions according to the first flow-cycle order or the second flow-cycle order. In some embodiments, at least one non-selected candidate sequence from the two or more different candidate sequences differs from the selected candidate sequence at two or more non-consecutive flow positions according to both the first flow-cycle order and the second flow-cycle order. In some embodiments, at least one non-selected candidate sequence from the two or more different candidate sequences differs from the selected candidate sequence at two or more consecutive flow positions according to the first flow-cycle order or the second flow-cycle order. In some embodiments, at least one non-selected candidate sequence from the two or more different candidate sequences differs from the selected candidate sequence at two or more consecutive flow positions according to both the first flow-cycle order and the second flow-cycle order. In some embodiments, at least one non-selected candidate sequence from the two or more different candidate sequences differs from the selected candidate sequence at 3 or more flow positions according to the first flow-cycle order or the second flow-cycle order. In some embodiments, at least one non-selected candidate sequence from the two or more different candidate sequences differs from the selected candidate sequence at 3 or more flow positions according to both the first flow-cycle order and the second flow-cycle order. In some embodiments, at least one non-selected candidate sequence from the two or more different candidate sequences differs from the selected candidate sequence at X base positions, and wherein the test sequencing data set associated with the test nucleic acid molecule differs from at least one non-selected candidate sequence from the two or more different candidate sequences at (X+2) or more flow positions according to the first flow-cycle order or the second flow-cycle order. In some embodiments, at least one non-selected candidate sequence from the two or more different candidate sequences differs from the selected candidate sequence at X base positions, and wherein the test sequencing data set associated with the test nucleic acid molecule differs from at least one non-selected candidate sequence from the two or more different candidate sequences at (X+2) or more flow positions according to both the first flow-cycle order and the second flow-cycle order. In some embodiments, the (X+2) flow position differences comprise differences between values substantially equal to zero and values substantially greater than zero. In some embodiments, at least one non-selected candidate sequence from the two or more different candidate sequences differs from the selected candidate sequence across one or more flow-cycles according to the first flow-cycle order or the second flow-cycle order. In some embodiments, at least one non-selected candidate sequence from the two or more different candidate sequences differs from the selected candidate sequence across one or more flow-cycles according to both the first flow-cycle order and the second flow-cycle order.

In some embodiments of the above method, the flow signals comprise a base count indicative of a number of bases of the test nucleic acid molecule sequenced at each flow position. In some embodiments, the flow signals comprise a statistical parameter indicative of a likelihood for at least one base count at each flow position, wherein the base count is indicative of a number of bases of the test nucleic acid molecule sequenced at the flow position. In some embodiments, the flow signals comprise a statistical parameter indicative of a likelihood for a plurality of base counts at each flow position, wherein each base count is indicative of a number of bases of the test nucleic acid molecule sequenced at the flow position. In some embodiments, determining the match score comprises, for each of the one or more different candidate sequences, selecting the statistical parameter at each flow position in the first test sequencing data set and the second test sequencing data set that corresponds with a base count of the candidate sequence at that flow position. In some embodiments of the above method, the method comprises, for the one or more different candidate sequences, generating a candidate sequencing data set comprising the base count of the candidate sequence at each flow position. In some embodiments, the candidate sequencing data set is generated in silico. In some embodiments, the match score is a combined value of the selected statistical parameters across the flow positions in the first test sequencing data set and the second test sequencing data set.

In some embodiments of the above method, at least a portion of the test nucleic acid molecules have different sequencing start positions.

In some embodiments of the above method, the method further comprises selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to the first flow-cycle order or the second flow cycle order, wherein the first flow-cycle order is different from the second flow cycle order, and wherein the flow positions corresponds to the nucleotide flows; wherein the one or more candidate sequences comprises the target sequence and the reference sequence. In some embodiments, the target short genetic variant is pre-selected prior to calling the presence or absence of the target short genetic variant in the test sample. In some embodiments, the target short genetic variant is selected after calling the presence or absence of the target short genetic variant in the test sample based on a confidence of the call. In some embodiments, the method further comprises generating a personalized biomarker panel for a subject associated with the test sample, the biomarker panel comprising the target short genetic variant present in the test sample. In some embodiments, the reference sequencing data set is obtained by determining an expected reference sequencing data set if the reference sequence was sequenced using non-terminating nucleotides provided in separate flows according to the first flow-cycle order or the second flow-cycle order. In some embodiments, the reference sequencing data set is obtained by determining an expected reference sequencing data set if the reference sequence was sequenced using non-terminating nucleotides provided in separate flows according to both the first flow-cycle order and the second flow-cycle order. In some embodiments, the target sequence differs from the reference sequence at two or more flow positions according to both the first flow-cycle order and the second flow-cycle order. In some embodiments, the target sequence differs from the reference sequence at two or more non-consecutive flow positions according to the first flow-cycle order or the second flow-cycle order. In some embodiments, the target sequence differs from the reference sequence at two or more non-consecutive flow positions according to both the first flow-cycle order and the second flow-cycle order. In some embodiments, the target sequence differs from the reference sequence at two or more consecutive flow positions according to the first flow-cycle order or the second flow-cycle order. In some embodiments, the target sequence differs from the reference sequence at two or more consecutive flow positions according to both the first flow-cycle order and the second flow-cycle order. In some embodiments, the target sequence differs from the reference sequence at three or more flow positions according to the first flow-cycle order or the second flow-cycle order. In some embodiments, the target sequence differs from the reference sequence at three or more flow positions according to both the first flow-cycle order and the second flow-cycle order. In some embodiments, the target sequence differs from the reference sequence across one or more flow-cycles according to the first flow-cycle order or the second flow-cycle order. In some embodiments, the target sequence differs from the reference sequence across one or more flow-cycles according to both the first flow-cycle order and the second flow-cycle order.

In some embodiments of the method described above, the first flow-cycle order or the second flow-cycle order comprises 4 separate flows repeated in the same order. In some embodiments, the first flow-cycle order or the second flow-cycle order comprises 5 or more separate flows repeated in the same order.

In some embodiments of the method described above, the method comprises sequencing the test nucleic acid molecule, comprising providing the non-terminating nucleotides in separate nucleotide flows according to the first flow-cycle order, extending a sequencing primer, and detecting the presence or absence of nucleotide incorporation into the sequencing primer after each nucleotide flow to generate the first test sequencing data set; removing the extended sequencing primer; and sequencing the same test nucleic acid molecule, comprising providing the non-terminating nucleotides in separate nucleotide flows according to the second flow-cycle order, extending a sequencing primer, and detecting the presence or absence of nucleotide incorporation into the sequencing primer after each nucleotide flow to generate the second test sequencing data set.

In some embodiments of the method described above, the method is a computer-implemented method. For example, in some embodiments, the computer-implemented method comprises receiving the one or more first sequencing data sets at one or more processors; receiving the one or more first sequencing data sets at the one or more processors; determining the match scores using the one or more processors; and calling the presence or absence of the target short genetic variant in the test sample using the one or more processors.

Also described herein is a system, comprising one or more processors; and a non-transitory computer-readable medium that stores one or more programs comprising instructions for implementing any of the methods described above.

In some embodiments of any of the methods or systems described above, the separate flows comprise a single base type.

In some embodiments of any of the methods or systems described above, at least one of the separate flows comprise 2 or 3 different base types.

In some embodiments of any of the methods or systems described above, the method comprises generating or updating a variant call file that indicates the presence, identity or absence of the short genetic variant in the test sample.

In some embodiments of any of the methods or systems described above, the method comprises generating a report that indicates the presence, identity, or absence of the short genetic variant in the test sample. In some embodiments, the report comprises a textual, probabilistic, numerical, or graphical output indicating the presence, identity, or absence of the short genetic variant in the test sample. In some embodiments, the method comprises providing the report to a patient or a healthcare representative of the patient.

In some embodiments of any of the methods or systems described above, the short genetic variant comprises a single nucleotide polymorphism.

In some embodiments of any of the methods or systems described above, the short genetic variant comprises an indel.

In some embodiments of any of the methods or systems described above, the test sample comprises fragmented DNA.

In some embodiments of any of the methods or systems described above, the test sample comprises cell-free DNA. In some embodiments, the cell-free DNA comprises circulating tumor DNA (ctDNA).

In some embodiments, a method of sequencing a nucleic acid molecule comprises hybridizing the nucleic acid molecule to a primer to form a hybridized template; extending the primer using labeled, non-terminating nucleotides provided in separate nucleotide flows according to a repeated flow-cycle order comprising five or more separate nucleotide flows; and detecting a signal from an incorporated labeled nucleotide or an absence of a signal as the primer is extended by the nucleotide flows. In some embodiments, the method comprises detecting the signal or absence of the signal after each nucleotide flow. In some embodiments, the method comprises sequencing a plurality of nucleic acid molecules. In some embodiments, the nucleic acid molecules in the plurality have different sequencing start positions with respect to a locus. In some embodiments, the test sample is cell-free DNA. In some embodiments, the cell-free DNA comprises circulating tumor DNA (ctDNA). In some embodiments, the flow-cycle order induces a signal change at more than two flow positions for 50% or more of possible SNP permutations at least 5% of random sequencing start positions. In some embodiments, the induced signal change is a change in signal intensity, or a new substantially zero (or new zero) or a new substantially non-zero (or new non-zero) signal. In some embodiments, the induced signal change is a new substantially zero (or new zero) or a new substantially non-zero (or new non-zero) signal. In some embodiments, the flow-cycle order has an efficiency of 0.6 or more base incorporations per flow.

BRIEF DESCRIPTION OF THE DRAWINGS

FIG. 1A shows sequencing data obtained by extending a primer with a sequence of TATGGTCGTCGA (SEQ ID NO: 1) using a repeated flow-cycle order of T-A-C-G. The sequencing data is representative of the extended primer strand, and sequencing information for the complementary template strand can be readily determined is effectively equivalent.

FIG. 1B shows the sequencing data shown in FIG. 1A with the most likely sequence, given the sequencing data, selected based on the highest likelihood at each flow position (as indicated by stars).

FIG. 1C shows the sequencing data shown in FIG. 1A with traces representing two different candidate sequences: TATGGTCATCGA (SEQ ID NO: 2) (closed circles) and TATGGTCGTCGA (SEQ ID NO: 1) (open circles). The likelihood that the sequencing data matches a given sequence can be determined as the product of the likelihood that each flow position matches the candidate sequence.

FIG. 2A shows an alignment of sequencing reads R1 (SEQ ID NO: 1), R2 (SEQ ID NO: 3), and R3 (SEQ ID NO: 4) (each represented by the sequence of an extended primer) aligned with two candidate sequences H1 (SEQ ID NO: 5) and H2 (SEQ ID NO: 6) (each represented by their complement). FIG. 2B shows sequencing data corresponding to R1 with traces representing H1 (closed circles) and H2 (open circles). FIG. 2C shows sequencing data corresponding to R2 with traces representing H1 (closed circles) and H2 (open circles). FIG. 2D shows sequencing data corresponding to R3 with traces representing H1 (closed circles) and H2 (open circles).

FIG. 4A shows sequencing data from a nucleic acid molecule having an extended primer sequence of TATGGTCGTCGA (SEQ ID NO: 1) obtained by sequencing the nucleic acid molecule using a first flow-cycle order (T-A-C-G), and FIG. 4B shows sequencing data obtained by sequencing the same nucleic acid molecule using a second flow-cycle order (A-G-C-T). Further, each FIG. 4A and FIG. 4B show traces from a first candidate sequence TATGGTCGTCGA (SEQ ID NO: 1) (closed circles) and a second candidate sequence TATGGTCATCGA (SEQ ID NO: 2) (open circles). As shown in FIG. 4A and FIG. 4B, differences in the flow-cycle order can drastically change the detected signal at a given flow position, and a more significant signal difference can be detected when using a better flow cycle for the context of the variant.

FIG. 8 shows sequencing data from a hypothetical nucleic acid molecule sequenced using a A-T-G-C flow cycle order. Traces can be generated using potential haplotype sequences TATGGTCG-TCGA (SEQ ID NO: 7) (H1) and TATGGTC-GATCG (SEQ ID NO: 8) (H2), with H1 having a 1 base deletion relative to H2. The sequencing data has a better match to the H2 candidate sequence, and no indel is called in this sequence.

In FIG. 9, the x-axis indicates the fraction of the flow phases (or fragmentation start positions), and the y-axis indicates the fraction of SNP permutations having induced a signal change at more than two flow positions.

DETAILED DESCRIPTION OF THE INVENTION

Figure 3:
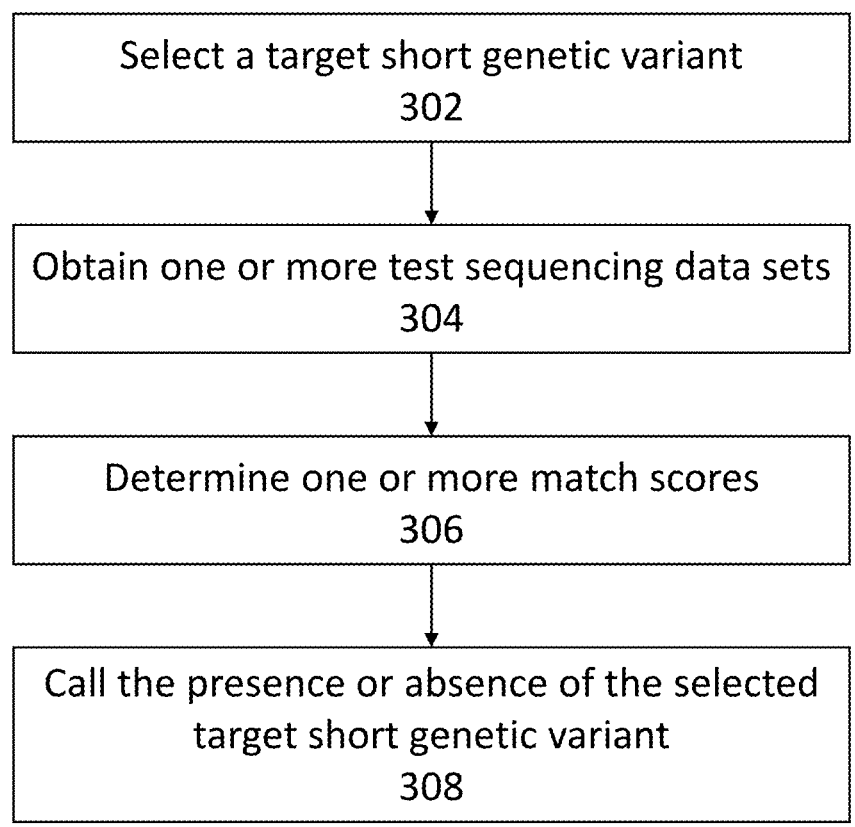
FIG. 3 shows a flow chart of an exemplary method for detecting a short genetic variant in a test sample.

Described herein are methods for detecting one or more short genetic variants, such as a single nucleotide polymorphism (SNP), a multi-nucleotide polymorphism (MNP), or an indel, in a test sample derived from a subject. Test sequencing data associated with test nucleic acid molecules from the test sample is analyzed to determine a match between the test sequencing data and another sequence (such as a test sequence, a candidate sequence (or candidate haplotype sequence and/or a reference sequence), which may be reflected by determining a match score that indicates the closeness of the match (e.g., a likelihood that, given the test sequencing data, that the test sequencing data arose from a nucleic acid molecule of the compared sequence). The match score can then be used to call the presence or identity, or absence, of the short genetic variant in the test sample.

The test sequencing data set is uniquely structured to provide a computationally efficient analysis. For example, the test sequencing data set can be generated by sequencing the test nucleic acid molecule using non-terminating nucleotides provided in separate nucleotide flows according to a flow-cycle order. The test sequencing data set for the nucleic acid molecule then includes flow signals at flow positions that each corresponds to a flow of a particular nucleotide.

Using this uniquely structured data set, the nucleic acid molecule (or molecules) can be analyzed in "flowspace" rather than "basespace" (also referred to as "nucleotide space" or "sequence space"). The flowspace data depend on additional information related to the flow-cycle order, which is not carried by basespace data. Analysis of data collected in flowspace provides at least two advantages over analysis of data converted to or collected in basespace. First, the most common variant type (substitution SNP) in the test nucleic acid molecule will result in two or more distinct flow signals (which may propagate for a full flow cycle, or more) when compared to a reference sequence in flowspace, whereas only one data signal is available when analyzing the sequences in basespace. That is, in basespace, each base position is associated with a single signal, and a variant base only affects the signal of the variant base and no adjacent signal. In flowspace, the variant may affect multiple flow positions and, for certain variants, the variant may induce a shift in subsequent flowgram signals relative to a reference sequence thereby creating in effect a continuing reinforcement of the variant detection. Second, the flowspace data can be analyzed to determine a match with one or more candidate flowspace sequences without a direct alignment between the sequence of the test nucleic acid molecule and the one or more candidate sequences. Sequence alignments are computationally expensive, and can be simplified using the match analysis described herein.

A multiple-signal indicator in flowspace for a given genetic variant increases the variant call accuracy over a single signal indicator that may be identified in basespace analysis. Further, a greater number of flow signal differences increases the likelihood a variant call will be detected. As further discussed herein, in certain circumstances it is desirable to call pre-selected variants with high confidence, and those variants and/or the flow order can be selected to ensure the desired number of flow signal differences are generated to confidently call the genetic variant. The sequencing data set for a nucleic acid molecule can be compared to a candidate sequence to determine a match score indicative of a likelihood that the test sequencing data set matches the candidate sequence.

Alignment of determined sequences to candidate sequences (such as candidate haplotype sequences) in base space is computationally expensive, and is currently the most computationally intensive step in the Genome Analysis Tool Kit (GATK) HaplotypeCaller. Within HaplotypeCaller, PairHMM aligns each sequencing read to each haplotype, and uses base qualities as an estimate of the error to determine the likelihood of the haplotypes given the sequencing read. However, the structure of the data set used with the methods described herein retains error mode likelihoods, which makes variant calling more computationally efficient. For example, a given genotype likelihood may be determined simply as the product of likelihoods in each flow position that aligns with the sequence having the genotype. The flowspace determined likelihood can replace the PairHMM module of the HaplotypeCaller for a more computationally efficient variant call.

The flow signal for any flow position in a sequencing data set is flow-order-dependent in that the flow order used to sequence the nucleic acid molecule at any base position can affect the flow signal at that position. As further described herein, this discovery can be taken advantage of in one or more manners. First, random fragmentation of nucleic acid molecules (either in vivo fragmentation, such as cell-free DNA, or in vitro fragmentation, such as by sonication or enzymatic digestion) that overlap at the same locus results in multiple different sequencing start sites (relative to the locus) for the nucleic acid molecules. In some cases, different flow contexts are available at the locus (e.g., when re-sequencing with a different flow order, or when using a quasi-periodic flow order). Accordingly, a variant at the locus may be accurately detected based on a single nucleic acid molecule with a high sensitivity flow signal for the variant (for example, with two or more flow signal differences compared to a reference or non-selected candidate sequence) even if other nucleic acid molecules result in a lower-confidence signal (for example, a single flow signal change). Second, a given nucleic acid molecule may be sequenced using a first flow order, and re-sequenced using a second (different) flow order, thus providing a different flow sequence context across the nucleic acid molecule. If the likelihood match of the nucleic acid molecule with a variant to a candidate sequence with the variant is low using one flow order, the likelihood match of the nucleic acid molecule to the candidate sequence may be high using the second flow order. Third, the flow order can be extended flow cycle (e.g., with more than four base types in a cycle), meaning that it is not simply a four flow periodic repeat of the four base types A, C, T and G. In some cases, the repeating unit is longer than four bases, such as a pattern comprising all possible two-base flow sequences (i.e., all X-Y pairs are within the repeating unit where X is all four bases and Y is each of the non-X bases) or three-base flow sequences (i.e., all possible X-Y-Z permutations are within the repeating unit). Fourth, a flow sequencing order may be selected to target a specific genetic variant.

In some embodiments, a method for detecting a short genetic variant in a test sample includes: (a) obtaining one or more test sequencing data sets, each test sequencing data set associated with a test nucleic acid molecule derived from the test sample, wherein the test sequencing data set was generated by sequencing the test nucleic acid molecule using non-terminating nucleotides provided in separate nucleotide flows according to a flow order, and wherein the test sequencing data set comprises flow signals at flow positions corresponding to the nucleotide flows; (b) determining, for each test nucleic acid molecule associated with a test sequencing data set, a match score indicative of a likelihood that the test sequencing data set matches one or more candidate sequences; and (c) calling, using the one or more determined match scores, the presence or absence of the target short genetic variant in the test sample.

In some embodiments, a method for detecting a short genetic variant in a test sample comprises (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions corresponds to the nucleotide flows; (b) obtaining one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample.

In some embodiments, a method for detecting a short genetic variant in a test sample includes (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

The methods described herein may be computer-implemented methods, and one or more steps of the method may be performed, for example, using one or more computer processors.

Also provided herein is a non-transitory computer-readable storage medium storing one or more programs, the one or more programs comprising instructions, which when executed by one or more processors of an electronic device, cause the electronic device to perform any one or more of the methods described herein.

Further described herein is an electronic device, comprising one or more processors, a memory, and one or more programs stored in the memory, the one or more programs configured to be executed by the one or more processors. The one or more programs may include instructions for performing any one or more of the methods described herein.

Also described herein are methods of sequencing nucleic acid molecules. For example, a method of sequencing a nucleic acid molecule may include: hybridizing the nucleic acid molecule to a primer to form a hybridized template; extending the primer using labeled, non-terminating nucleotides provided in separate nucleotide flows according to a repeated flow-cycle order comprising five or more separate nucleotide flows; and detecting a signal from an incorporated labeled nucleotide or an absence of a signal as the primer is extended by the nucleotide flows.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

"Expected sequencing data" or "expected sequencing data set" for a given sequence refers to calculated sequencing data that would be generated if the sequence were sequenced using non-terminating nucleotides provided in separate nucleotide flows according to a flow order. The expected sequencing data set or expected sequencing data set can be determined, for example, by computer modeling (i.e., in silico).

A "flow order" refers to the order of separate nucleotide flows used to sequence a nucleic acid molecule using non-terminating nucleotides. The flow order may be divided into cycles of repeating units, and the flow order of the repeating units is termed a "flow-cycle order." A "flow position" refers to the sequential position of a given separate nucleotide flow during the sequencing process.

The terms "individual," "patient," and "subject" are used synonymously, and refers to an animal including a human.

The term "label," as used herein, refers to a detectable moiety that is coupled to or may be coupled to another moiety, for example, a nucleotide or nucleotide analog. The label can emit a signal or alter a signal delivered to the label so that the presence or absence of the label can be detected. In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase, or protease). In some embodiments, the label is a fluorophore.

A "non-terminating nucleotide" is a nucleic acid moiety that can be attached to a 3' end of a polynucleotide using a polymerase or transcriptase, and that can have another non-terminating nucleic acid attached to it using a polymerase or transcriptase without the need to remove a protecting group or reversible terminator from the nucleotide. Naturally occurring nucleic acids are a type of non-terminating nucleic acid. Non-terminating nucleic acids may be labeled or unlabeled.

A "nucleotide flow" refers to a set of one or more non-terminating nucleotides (which may be labeled or a portion of which may be labeled).

A "short genetic variant" is used herein to describe a genetic polymorph (i.e., mutation) 10 consecutive bases in length or less (i.e., 10, 9, 8, 7, 6, 5, 4, 3, 2, or 1 base(s) in length). The term includes single nucleotide polymorphisms (SNPs), multi-nucleotide polymorphisms (MNPs), and indels 10 consecutive bases in length or less.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

Some of the analytical methods described herein include mapping sequences to a reference sequence, determining sequence information, and/or analyzing sequence information. It is well understood in the art that complementary sequences can be readily determined and/or analyzed, and that the description provided herein encompasses analytical methods performed in reference to a complementary sequence.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The figures illustrate processes according to various embodiments. In the exemplary processes, some blocks are, optionally, combined, the order of some blocks is, optionally, changed, and some blocks are, optionally, omitted. In some examples, additional steps may be performed in combination with the exemplary processes. Accordingly, the operations as illustrated (and described in greater detail below) are exemplary by nature and, as such, should not be viewed as limiting.

The disclosures of all publications, patents, and patent applications referred to herein are each hereby incorporated by reference in their entireties. To the extent that any reference incorporated by reference conflicts with the instant disclosure, the instant disclosure shall control.

Flow Sequencing Methods

Sequencing data can be generated using a flow sequencing method that includes extending a primer bound to a template polynucleotide molecule according to a pre-determined flow cycle where, in any given flow position, a single type of nucleotide is accessible to the extending primer. In some embodiments, at least some of the nucleotides of the particular type include a label, which upon incorporation of the labeled nucleotides into the extending primer renders a detectable signal. The resulting sequence by which such nucleotides are incorporated into the extended primer should be the reverse complement of the sequence of the template polynucleotide molecule. In some embodiments, for example, sequencing data is generated using a flow sequencing method that includes extending a primer using labeled nucleotides, and detecting the presence or absence of a labeled nucleotide incorporated into the extending primer. Flow sequencing methods may also be referred to as "natural sequencing-by-synthesis," or "non-terminated sequencing-by-synthesis" methods. Exemplary methods are described in U.S. Pat. No. 8,772,473, which is incorporated herein by reference in its entirety. While the following description is provided in reference to flow sequencing methods, it is understood that other sequencing methods may be used to sequence all or a portion of the sequenced region. For example, the sequencing data discussed herein can be generated using pyrosequencing methods.

Flow sequencing includes the use of nucleotides to extend the primer hybridized to the polynucleotide. Nucleotides of a given base type (e.g., A, C, G, T, U, etc.) can be mixed with hybridized templates to extend the primer if a complementary base is present in the template strand. The nucleotides may be, for example, non-terminating nucleotides. When the nucleotides are non-terminating, more than one consecutive base can be incorporated into the extending primer strand if more than one consecutive complementary base is present in the template strand. The non-terminating nucleotides contrast with nucleotides having 3' reversible terminators, wherein a blocking group is generally removed before a successive nucleotide is attached. If no complementary base is present in the template strand, primer extension ceases until a nucleotide that is complementary to the next base in the template strand is introduced. At least a portion of the nucleotides can be labeled so that incorporation can be detected. Most commonly, only a single nucleotide type is introduced at a time (i.e., discretely added), although two or three different types of nucleotides may be simultaneously introduced in certain embodiments. This methodology can be contrasted with sequencing methods that use a reversible terminator, wherein primer extension is stopped after extension of every single base before the terminator is reversed to allow incorporation of the next succeeding base.

The nucleotides can be introduced at a flow order during the course of primer extension, which may be further divided into flow cycles. The flow cycles are a repeated order of nucleotide flows, and may be of any length. Nucleotides are added stepwise, which allows incorporation of the added nucleotide to the end of the sequencing primer of a complementary base in the template strand is present. Solely by way of example, the flow order of a flow cycle may be A-T-G-C, or the flow cycle order may be A-T-C-G. Alternative orders may be readily contemplated by one skilled in the art. The flow cycle order may be of any length, although flow cycles containing four unique base type (A, T, C, and G in any order) are most common. In some embodiments, the flow cycle includes 5, 6, 7, 8, 9, 10, 11, 12, 13, 14, 15, 16, 17, 18, 19, 20 or more separate nucleotide flows in the flow cycle order. Solely by way of example, the flow cycle order may be T-C-A-C-G-A-T-G-C-A-T-G-C-T-A-G, with these 16 separately provided nucleotides provided in this flow-cycle order for several cycles. Between the introductions of different nucleotides, unincorporated nucleotides may be removed, for example by washing the sequencing platform with a wash fluid.

A polymerase can be used to extend a sequencing primer by incorporating one or more nucleotides at the end of the primer in a template-dependent manner. In some embodiments, the polymerase is a DNA polymerase. The polymerase may be a naturally occurring polymerase or a synthetic (e.g., mutant) polymerase. The polymerase can be added at an initial step of primer extension, although supplemental polymerase may optionally be added during sequencing, for example with the stepwise addition of nucleotides or after a number of flow cycles. Exemplary polymerases include a DNA polymerase, an RNA polymerase, a thermostable polymerase, a wild-type polymerase, a modified polymerase, Bst DNA polymerase, Bst 2.0 DNA polymerase Bst 3.0 DNA polymerase, Bsu DNA polymerase, E. coli DNA polymerase I, T7 DNA polymerase, bacteriophage T4 DNA polymerase 129 (phi29) DNA polymerase, Taq polymerase, Tth polymerase, Tli polymerase, Pfu polymerase, and SeqAmp DNA polymerase.

The introduced nucleotides can include labeled nucleotides when determining the sequence of the template strand, and the presence or absence of an incorporated labeled nucleic acid can be detected to determine a sequence. The label may be, for example, an optically active label (e.g., a fluorescent label) or a radioactive label, and a signal emitted by or altered by the label can be detected using a detector. The presence or absence of a labeled nucleotide incorporated into a primer hybridized to a template polynucleotide can be detected, which allows for the determination of the sequence (for example, by generating a flowgram). In some embodiments, the labeled nucleotides are labeled with a fluorescent, luminescent, or other light-emitting moiety. In some embodiments, the label is attached to the nucleotide via a linker. In some embodiments, the linker is cleavable, e.g., through a photochemical or chemical cleavage reaction. For example, the label may be cleaved after detection and before incorporation of the successive nucleotide(s). In some embodiments, the label (or linker) is attached to the nucleotide base, or to another site on the nucleotide that does not interfere with elongation of the nascent strand of DNA. In some embodiments, the linker comprises a disulfide or PEG-containing moiety.

In some embodiment, the nucleotides introduced include only unlabeled nucleotides, and in some embodiments the nucleotides include a mixture of labeled and unlabeled nucleotides. For example, in some embodiments, the portion of labeled nucleotides compared to total nucleotides is about 90% or less, about 80% or less, about 70% or less, about 60% or less, about 50% or less, about 40% or less, about 30% or less, about 20% or less, about 10% or less, about 5% or less, about 4% or less, about 3% or less, about 2.5% or less, about 2% or less, about 1.5% or less, about 1% or less, about 0.5% or less, about 0.25% or less, about 0.1% or less, about 0.05% or less, about 0.025% or less, or about 0.01% or less. In some embodiments, the portion of labeled nucleotides compared to total nucleotides is about 100%, about 95% or more, about 90% or more, about 80% or more about 70% or more, about 60% or more, about 50% or more, about 40% or more, about 30% or more, about 20% or more, about 10% or more, about 5% or more, about 4% or more, about 3% or more, about 2.5% or more, about 2% or more, about 1.5% or more, about 1% or more, about 0.5% or more, about 0.25% or more, about 0.1% or more, about 0.05% or more, about 0.025% or more, or about 0.01% or more. In some embodiments, the portion of labeled nucleotides compared to total nucleotides is about 0.01% to about 100%, such as about 0.01% to about 0.025%, about 0.025% to about 0.05%, about 0.05% to about 0.1%, about 0.1% to about 0.25%, about 0.25% to about 0.5%, about 0.5% to about 1%, about 1% to about 1.5%, about 1.5% to about 2%, about 2% to about 2.5%, about 2.5% to about 3%, about 3% to about 4%, about 4% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to less than 100%, or about 90% to about 100%.

Prior to generating the sequencing data, the polynucleotide is hybridized to a sequencing primer to generate a hybridized template. The polynucleotide may be ligated to an adapter during sequencing library preparation. The adapter can include a hybridization sequence that hybridizes to the sequencing primer. For example, the hybridization sequence of the adapter may be a uniform sequence across a plurality of different polynucleotides, and the sequencing primer may be a uniform sequencing primer. This allows for multiplexed sequencing of different polynucleotides in a sequencing library.

The polynucleotide may be attached to a surface (such as a solid support) for sequencing. The polynucleotides may be amplified (for example, by bridge amplification or other amplification techniques) to generate polynucleotide sequencing colonies. The amplified polynucleotides within the cluster are substantially identical or complementary (some errors may be introduced during the amplification process such that a portion of the polynucleotides may not necessarily be identical to the original polynucleotide). Colony formation allows for signal amplification so that the detector can accurately detect incorporation of labeled nucleotides for each colony. In some cases, the colony is formed on a bead using emulsion PCR and the beads are distributed over a sequencing surface. Examples for systems and methods for sequencing can be found in U.S. Pat. No. 10,344,328, which is incorporated herein by reference in its entirety.

The primer hybridized to the polynucleotide is extended through the nucleic acid molecule using the separate nucleotide flows according to the flow order (which may be cyclical according to a flow-cycle order), and incorporation of a nucleotide can be detected as described above, thereby generating the sequencing data set for the nucleic acid molecule.

Primer extension using flow sequencing allows for long-range sequencing on the order of hundreds or even thousands of bases in length. The number of flow steps or cycles can be increased or decreased to obtain the desired sequencing length. Extension of the primer can include one or more flow steps for stepwise extension of the primer using nucleotides having one or more different base types. In some embodiments, extension of the primer includes between 1 and about 1000 flow steps, such as between 1 and about 10 flow steps, between about 10 and about 20 flow steps, between about 20 and about 50 flow steps, between about 50 and about 100 flow steps, between about 100 and about 250 flow steps, between about 250 and about 500 flow steps, or between about 500 and about 1000 flow steps. The flow steps may be segmented into identical or different flow cycles. The number of bases incorporated into the primer depends on the sequence of the sequenced region, and the flow order used to extend the primer. In some embodiments, the sequenced region is about 1 base to about 4000 bases in length, such as about 1 base to about 10 bases in length, about 10 bases to about 20 bases in length, about 20 bases to about 50 bases in length, about 50 bases to about 100 bases in length, about 100 bases to about 250 bases in length, about 250 bases to about 500 bases in length, about 500 bases to about 1000 bases in length, about 1000 bases to about 2000 bases in length, or about 2000 bases to about 4000 bases in length.

The polynucleotides used in the methods described herein may be obtained from any suitable biological source, for example a tissue sample, a blood sample, a plasma sample, a saliva sample, a fecal sample, or a urine sample. The polynucleotides may be DNA or RNA polynucleotides. In some embodiments, RNA polynucleotides are reverse transcribed into DNA polynucleotides prior to hybridizing the polynucleotide to the sequencing primer. In some embodiments, the polynucleotide is a cell-free DNA (cfDNA), such as a circulating tumor DNA (ctDNA) or a fetal cell-free DNA. The nucleic acid molecules may be randomly fragmented, for example in vivo (e.g., as in cfDNA) or in vitro (for example, by sonication or enzymatic fragmentation).

Libraries of the polynucleotides may be prepared through known methods. In some embodiments, the polynucleotides may be ligated to an adapter sequence. The adapter sequence may include a hybridization sequence that hybridized to the primer extended during the generated of the coupled sequencing read pair.

In some embodiments, the sequencing data is obtained without amplifying the nucleic acid molecules prior to establishing sequencing colonies (also referred to as sequencing clusters). Methods for generating sequencing colonies include bridge amplification or emulsion PCR. Methods that rely on shotgun sequencing and calling a consensus sequence generally label nucleic acid molecules using unique molecular identifiers (UMIs) and amplify the nucleic acid molecules to generate numerous copies of the same nucleic acid molecules that are independently sequenced. The amplified nucleic acid molecules can then be attached to a surface and bridge amplified to generate sequencing clusters that are independently sequenced. The UMIs can then be used to associate the independently sequenced nucleic acid molecules. However, the amplification process can introduce errors into the nucleic acid molecules, for example due to the limited fidelity of the DNA polymerase. In some embodiments, the nucleic acid molecules are not amplified prior to amplification to generate colonies for obtaining sequencing data. In some embodiments, the nucleic acid sequencing data is obtained without the use of unique molecular identifiers (UMIs).

Sequencing Data Sets and Variant Detection

Sequencing data can be generated based on the detection of an incorporated nucleotide and the order of nucleotide introduction. Take, for example, the flowing extended sequences (i.e., each reverse complement of a corresponding template sequence): CTG, CAG, CCG, CGT, and CAT (assuming no preceding sequence or subsequent sequence subjected to the sequencing method), and a repeating flow cycle of T-A-C-G (that is, sequential addition of T, A, C, and G nucleotides in repeating cycles). A particular type of nucleotides at a given flow position would be incorporated into the primer only if a complementary base is present in the template polynucleotide. An exemplary resulting flowgram is shown in Table 1, where 1 indicates incorporation of an introduced nucleotide and 0 indicates no incorporation of an introduced nucleotide. The flowgram can be used to derive the sequence of the template strand. For example, the sequencing data (e.g., flowgram) discussed herein represent the sequence of the extended primer strand, and the reverse complement of which can readily be determined to represent the sequence of the template strand. An asterisk (*) in Table 1 indicates that a signal may be present in the sequencing data if additional nucleotides are incorporated in the extended sequencing strand (e.g., a longer template strand).

TABLE 1

| | Cycle 1 | | | | Cycle 2 | | | | Cycle 3 | | | |
| --- | --- | --- | --- | --- | --- | --- | --- | --- | --- | --- | --- | --- |
| | | | | | Flow Position | | | | | | | |
| | 1 | 2 | 3 | 4 | 5 | 6 | 7 | 8 | 9 | 10 | 11 | 12 |
| | | | | | Base in Flow | | | | | | | |
| | T | A | C | G | T | A | C | G | T | A | C | G |
| Extended sequence: CTG | 0 | 0 | 1 | 0 | 1 | 0 | 0 | 1 | * | * | * | * |
| Extended sequence: CAG | 0 | 0 | 1 | 0 | 0 | 1 | 0 | 1 | * | * | * | * |
| Extended sequence: CCG | 0 | 0 | 2 | 1 | * | * | * | * | * | * | * | * |
| Extended sequence: CGT | 0 | 0 | 1 | 1 | 1 | * | * | * | * | * | * | * |
| Extended sequence: CAT | 0 | 0 | 1 | 0 | 0 | 1 | 0 | 0 | 1 | * | * | * |

The flowgram may be binary or non-binary. A binary flowgram detects the presence (1) or absence (0) of an incorporated nucleotide. A non-binary flowgram can more quantitatively determine a number of incorporated nucleotides from each stepwise introduction. For example, an extended sequence of CCG would include incorporation of two C bases in the extending primer within the same C flow (e.g., at flow position 3), and signals emitted by the labeled base would have an intensity greater than an intensity level corresponding to a single base incorporation. This is shown in Table 1. The non-binary flowgram also indicates the presence or absence of the base, and can provide additional information including the number of bases likely incorporated into each extending primer at the given flow position. The values do not need to be integers. In some cases, the values can be reflective of uncertainty and/or probabilities of a number of bases being incorporated at a given flow position.

In some embodiments, the sequencing data set includes flow signals representing a base count indicative of the number of bases in the sequenced nucleic acid molecule that are incorporated at each flow position. For example, as shown in Table 1, the primer extended with a CTG sequence using a T-A-C-G flow cycle order has a value of 1 at position 3, indicating a base count of 1 at that position (the 1 base being C, which is complementary to a G in the sequenced template strand). Also in Table 1, the primer extended with a CCG sequence using the T-A-C-G flow cycle order has a value of 2 at position 3, indicating a base count of 2 at that position for the extending primer during this flow position. Here, the 2 bases refer to the C-C sequence at the start of the CCG sequence in the extending primer sequence, and which is complementary to a G-G sequence in the template strand.

Figures 1A, 1B:
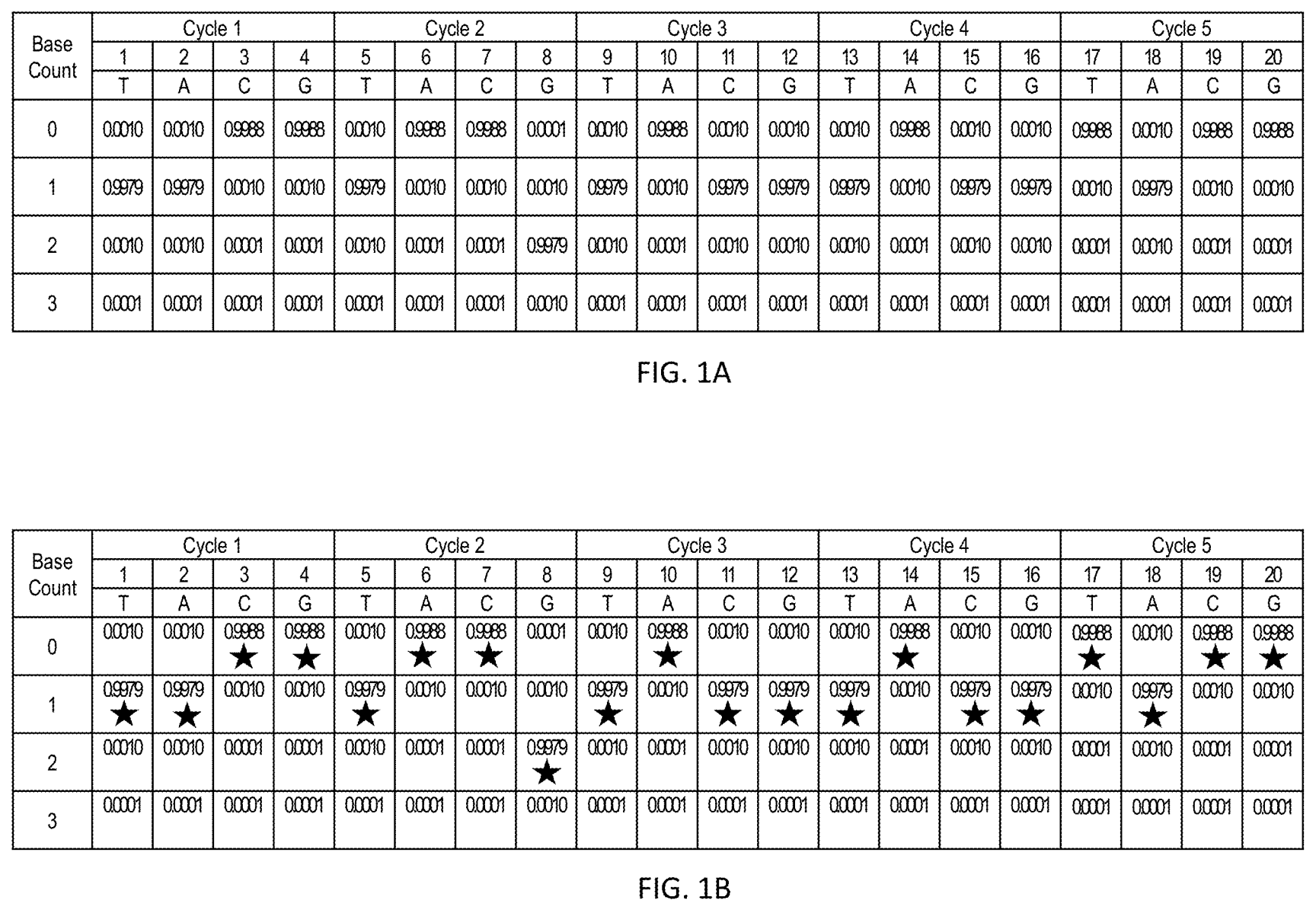

The flow signals in the sequencing data set may include one or more statistical parameters indicative of a likelihood or confidence interval for one or more base counts at each flow position. In some embodiments, the flow signal is determined from an analog signal that is detected during the sequencing process, such as a fluorescent signal of the one or more bases incorporated into the sequencing primer during sequencing. In some cases, the analog signal can be processed to generate the statistical parameter. For example, a machine learning algorithm can be used to correct for context effects of the analog sequencing signal as described in published International patent application WO 2019084158 A1, which is incorporated by reference herein in its entirety. Although an integer number of zero or more bases are incorporated at any given flow position, a given analog signal many not perfectly match with the analog signal. Therefore, given the detected signal, a statistical parameter indicative of the likelihood of a number of bases incorporated at the flow position can be determined. Solely by way of example, for the CCG sequence in Table 1, the likelihood that the flow signal indicates 2 bases incorporated at flow position 3 may be 0.999, and the likelihood that the flow signal indicates 1 base incorporated at flow position 3 may be 0.001. The sequencing data set may be formatted as a sparse matrix, with a flow signal including a statistical parameter indicative of a likelihood for a plurality of base counts at each flow position. Solely by way of example, a primer extended with a sequence of TATGGTCGTCGA (SEQ ID NO: 1) using a repeating flow-cycle order of T-A-C-G may result in a sequencing data set shown in FIG. 1A. The statistical parameter or likelihood values may vary, for example, based on the noise or other artifacts present during detection of the analog signal during sequencing. In some embodiments, if the statistical parameter or likelihood is below a predetermined threshold, the parameter may be set to a predetermined non-zero value that is substantially zero (i.e., some very small value or negligible value) to aid the statistical analysis further discussed herein, wherein a true zero value may give rise to a computational error or insufficiently differentiate between levels of unlikelihood, e.g. very unlikely (0.0001) and inconceivable (0).

A value indicative of the likelihood of the sequencing data set for a given sequence can be determined from the sequencing data set without a sequence alignment. For example the most likely sequence, given the data, can be determined by selecting the base count with the highest likelihood at each flow position, as shown by the stars in FIG. 1B (using the same data shown in FIG. 1A). Thus, the sequence of the primer extension can be determined according to the most likely base count at each flow position: TATGGTCGTCGA (SEQ ID NO: 1). From this, the reverse complement (i.e., the template strand) can be readily determined. Further, the likelihood of this sequencing data set, given the TATGGTCGTCGA (SEQ ID NO: 1) sequence (or the reverse complement), can be determined as the product of the selected likelihood at each flow position.

The sequencing data set associated with a nucleic acid molecule can be compared to one or more (e.g., 2, 3, 4, 5, 6 or more) possible candidate sequences. A close match (based on match score, as discussed below) between the sequencing data set and a candidate sequence indicates that it is likely the sequencing data set arose from a nucleic acid molecule having the same sequence as the closely matched candidate sequence. In some embodiments, the sequence of the sequenced nucleic acid molecule may be mapped to a reference sequence (for example using a Burrows-Wheeler Alignment (BWA) algorithm or other suitable alignment algorithm) to determine a locus (or one or more loci) for the sequence. As discussed above, the sequencing data set in flowspace can be readily converted to basespace (or vice versa, if the flow order is known), and the mapping may be done in flowspace or basespace. The locus (or loci) corresponding with the mapped sequence can be associated with one or more variant sequences, which can operate as the candidate sequences (or haplotype sequences) for the analytical methods described herein. One advantage of the methods described herein is that the sequence of the sequenced nucleic acid molecule does not need to be aligned with each candidate sequence using an alignment algorithm in some cases, which is generally computationally expensive. Instead, a match score can be determined for each of the candidate sequences using the sequencing data in flowspace, a more computationally efficient operation.

A match score indicates how well the sequencing data set supports a candidate sequence. For example, a match score indicative of a likelihood that the sequencing data set matches a candidate sequence can be determined by selecting a statistical parameter (e.g., likelihood) at each flow position that corresponds with the base count that flow position, given the expected sequencing data for the candidate sequence. The product of the selected statistical parameter can provide the match score. For example, assume the sequencing data set shown in FIG. 1A for an extended primer, and a candidate primer extension sequence of TATGGTCATCGA (SEQ ID NO: 2). FIG. 1C (showing the same sequencing data set in FIG. 1A) shows a trace for the candidate sequence (solid circles). As a comparison, the trace for the TATGGTCGTCGA (SEQ ID NO: 1) sequence (see FIG. 1B) is shown in FIG. 1C using open circles. The match score indicative of the likelihood that the sequencing data matches a first candidate sequence TATGGTCATCGA (SEQ ID NO: 2) is substantially different from the match score indicative of the likelihood that the sequencing data matches a second candidate sequence TATGGTCGTCGA (SEQ ID NO: 1), even though the sequences vary only by a single base variation. As seen in FIG. 1C, the differences between the traces is observed at flow position 12, and propagates for at least 9 flow positions (and potentially longer, if the sequencing data extended across additional flow positions). This continued propagation across one or more flow cycles may be referred to as a "flow shift" or a "cycle shift," and is generally a very unlikely event if the sequencing data set matches the candidate sequence.

A match score between each sequencing data set and candidate sequences (or each candidate sequence) can then be determined. For example, a likelihood that a sequencing data set matches a give candidate sequence $L(R_j|H_t)$ can be determined using (for example, product of) the likelihood of the selected base count at each flow position for the given candidate sequence.

The match score can be used to classify the test sequencing data and/or the nucleic acid molecule associated with the test sequencing data. The classifier can indicate that the nucleic acid molecule includes the variant (e.g., the variant included in the candidate sequence), that the nucleic acid molecule does not include the variant, or can indicate a null call. A null call neither indicates the presence or absence of the variant in the nucleic acid molecule associated with the test sequencing data, but instead indicates that the match score cannot be used to make a call with the desired statistical confidence. The test sequencing data or nucleic acid molecule may be classified as having the variant, for example, if the match score is above a desired confidence threshold. Conversely, the test sequencing data or nucleic acid molecule may be classified as not having the variant, for example, if the match score is below a desired confidence threshold.

The above analysis may be applied to select a candidate sequence from two or more different candidate sequences. The match score indicative of a likelihood that the sequencing data set matches each candidate sequence can be determined. For example, the statistical parameter at each flow position in the sequencing data set that corresponds with a base count of the candidate sequence at that flow position can be selected for each candidate sequence. In some embodiments, this analysis includes generating expected sequencing data for the candidate sequencing assuming the candidate sequence is sequenced using the same flow order used to generate the sequencing data set for the sequenced test nucleic acid molecule. This may be generated by sequencing a nucleic acid molecule with the candidate sequence, or by generating the candidate sequencing data set in silico based on the candidate sequence and the flow order. Exemplary candidate sequencing data sets are shown below the test data sequencing data set in FIG. 1C, with the first candidate sequence (TATGGTCATCGA (SEQ ID NO: 2)) corresponding to the solid circles trace and the second candidate sequence (TATGGTCGTCGA (SEQ ID NO: 1)) corresponding to the open circle trace. In some embodiments, for example, if a match score is determined for two or more different candidate sequences, the test sequencing data or the nucleic acid molecule may be classified as having the variant of one of the two or more candidate sequences, not having the variant of one of the two or more candidate sequence, or a null call may be made between the two or more candidate sequences (for example, if a call cannot be made for any of the candidate sequences or if the match score indicates two or more different variants at the same locus).

Once the match score for the sequencing data set is determined for the candidate sequences, the candidate sequence having the short genetic variant can be selected based on the match score (for example, the candidate sequence that results in a match score with the highest likelihood match from among the two or more candidate sequences). The short genetic variant can be, for example, a variant or mutation found within a subpopulation of individuals or a variant or mutation unique to a single or specific individual. The short genetic variants may be germline variants or somatic variants. The sequencing data arising from the sequence nucleic acid molecule having the short genetic variant will match the candidate sequence having the short genetic variant, and that candidate sequence can be selected, while the rejected (or non-selected) candidate sequence(s) do not include the short genetic variant as indicated by the less likelihood match (based on the determined match scores for those candidate sequences). The non-selected candidate sequence may differ from the selected candidate sequence (which best matches the sequenced nucleic acid molecule sequencing data set) at two or more flow positions, which may be two or more consecutive flow positions or two or more non-consecutive flow positions. In some embodiments, the non-selected candidate sequence differs from the selected candidate sequence at 3 or more, 4 or more, 5 or more, 6 or more, 7 or more, 8 or more, 9 or more, or 10 or more flow positions. In some embodiments, non-selected candidate sequence differs from the selected candidate sequence across 1 or more, 2 or more, 3 or more, 4 or more, or 5 or more flow cycles. In some embodiments, the non-selected candidate sequence differs from the selected candidate sequence at X base positions, wherein the sequencing data set associated with the sequence nucleic acid molecule differs from the non-selected candidate sequence at (X+2) or more flow positions. An increase in the number of different flow positions between the selected and the non-selected candidate sequence, wherein the sequenced nucleic acid molecule sequencing data set best matches the selected candidate sequence, lowers the likelihood that the sequenced nucleic acid molecule sequencing data set resulted from sequencing a nucleic acid molecule with the non-selected candidate sequence.

The likelihood that the sequencing data set for a sequenced nucleic acid molecule matches a non-selected candidate sequence is preferably low, such as less than 0.05, less than 0.04, less than 0.03, less than 0.02, less than 0.01, less than 0.005, less than 0.001, less than 0.0005, or less than 0.0001. The likelihood that the sequencing data set for a sequenced nucleic acid molecule matches a selected candidate sequence is preferably high, such as greater than 0.95, greater than 0.96, greater than 0.97, greater than 0.98, greater than 0.99, greater than 0.995, or greater than 0.999.

Figures 2C, 2D:
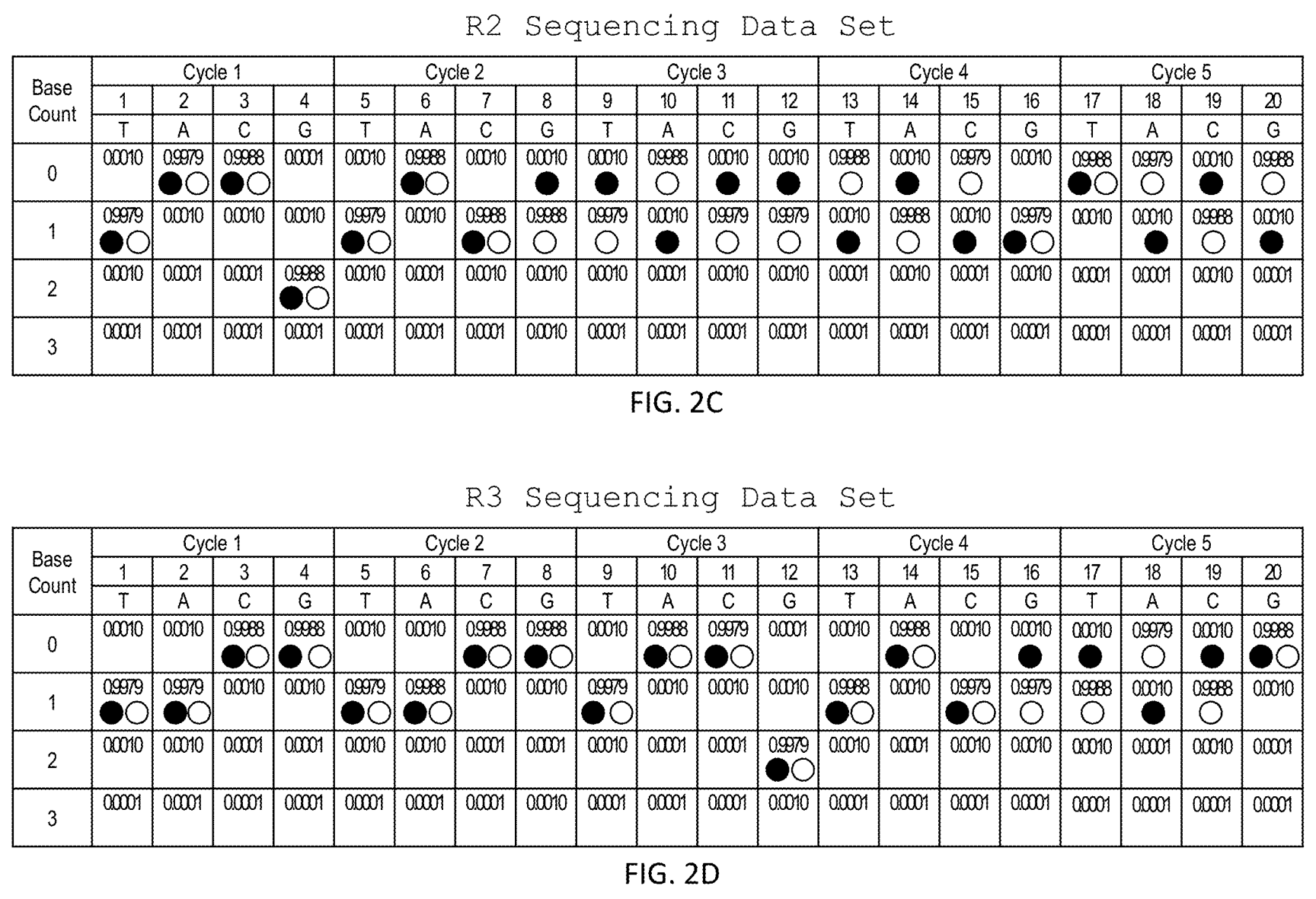

The method for detecting a short genetic variant in a test sample may, in some embodiments, include analyzing a plurality of test sequencing data sets, with each test sequencing data set being associated with a separate test nucleic acid molecule in the test sample. The nucleic acid molecules at least partially overlap at a locus, for example if the sequences of the nucleic acid molecules were aligned to a reference sequence. At least a portion of the nucleic acid molecules may have different sequencing start positions (with respect to a locus), which results in different flow positions for a given base within the sequence and/or a different flow order context. In this manner, the same candidate sequences can be used to analyze the test sequencing data sets in the plurality. For each candidate sequence, a match score indicative of a likelihood that the plurality of test sequencing data sets matches the candidate sequence can be determined, and the candidate sequence having the highest likelihood match (and thus, including the short genetic variant) can be selected. An exemplary analysis for detecting a short genetic variant using a plurality of test sequencing data sets is shown in FIGS. 2A-2D. In FIG. 2A, the sequence corresponding to three sequenced test nucleic acid molecules (R1, R2, and R3, each represented by the sequence of the extended primer) are aligned to a reference sequence at an overlapping locus associated with two candidate sequences (H1 and H2). FIG. 2B, FIG. 2C, and FIG. 2D show exemplary sequencing data sets for R1, R2, and R3, respectively, along with the selected statistical parameter at each flow position in the sequencing data set that corresponds with a base of H1 (closed circle) or H2 (open circle).

The presence (or identity) or absence of a short genetic variant can be called for the test sample using one or more determined match scores. In some embodiments, for example, a single nucleic acid molecule (or associated test sequencing data set) classified as having the variant may be sufficient to call the presence, identity, or absence of the variant, for example if the match score indicates a match with the candidate sequence with a desired or pre-set confidence. In some embodiments, an predetermined number (e.g., 1 or more, 2 or more, 3 or more, 4 or more, 5 or more, etc.) of nucleic acid molecules (or test sequencing data sets associated with nucleic acid molecules) are classified as having the variant before the variant is called for the test sample. In some embodiments, the number of nucleic acid molecules (or test sequencing data sets associated with nucleic acid molecules) is dynamically selected depending on the match scores; for example, a single nucleic acid molecule classified as having the variant with a high confidence match score may be used to call the variant, or two or more nucleic acid molecules classified as having the variant with lower confidence match scores may be used to call the variant.

Optionally, the separate match scores for sequencing data sets are collectively analyzed to determine a match score for the plurality of test sequencing data sets. For example, once the match score for each test sequencing data set for each candidate sequence is determined using the methods described herein, the match score indicative of a likelihood that the plurality of test sequencing data sets matches the candidate sequences can be determined using known Bayesian methods, for example, using the HaplotypeCaller algorithm included in the Genome Analysis Toolkit (GATK), and the candidate sequence with the highest likelihood match can be selected. See, e.g., DePristo et al., *A framework for variation discovery and genotyping using next-generation DNA sequencing data*, Nature Genetics 43, 491-498 (2011); and Poplin et al., *Scaling accurate genetic variant discovery to tens of thousands of samples*, bioRxiv, www.biorxiv.org/content/10.1101/201178v3 (Jul. 24, 2018); Hwang et al., *Systematic comparison of variant calling pipelines using gold standard personal exome variants*, Scientific Reports, vol. 5, no. 17875 (2015); the contents of each of which are incorporated herein.

Selection of a Target Variant and/or Flow-Cycle Order

Target short genetic variants may be selected, for example to act as a basis for selecting a flow order and/or candidate sequences (i.e., by pre-selecting the target short genetic variant), or for a downstream analysis. The downstream analysis may include, for example, assembling a biomarker panel comprising an identified short genetic variant. The biomarker panel can be personalized for the individual subject associated with the test sample. By way of example, the biomarker panel may include one or more short genetic variants associated with a disease (for example a cancer), for example a variant signature. In another example, the biomarker panel is personalized for the subject, includes one or more short genetic variants previously detected in a sample from the subject, which may be attributed to a disease (such as cancer) in the subject.

The methods for identifying a short genetic variant as described herein may be particularly useful when one or more target short genetic variants are preselected. The limit of detection (LOD) for a given short genetic variant can depend on the sequence context of the short genetic variant (e.g., the sequence of the nucleic acid molecule flanking the target short genetic variant locus) and the flow order (or flow cycle order) used to sequence the nucleic acid molecule and generate the sequencing data set for the nucleic acid molecule. That is, using a given flow order, short genetic variant, and short genetic variant context, the number of flow position variances in flow space a nucleic acid molecule having the short genetic variant and a nucleic acid molecule not having the short genetic variant (e.g., a reference sequence) can be determined. This allows for the selection of particularly sensitive variants or the selection of a flow order that can detect a particular variant with high sensitivity. A target sequencing data set associated with a target sequence comprising the target short genetic variant can be compared to a reference sequencing data set associated with a reference sequence that does not have the target short genetic variant to determine a number of flow position differences exist between the target sequence and the reference sequence. That is, the reference sequence is identical to the target sequence except for the target short genetic variant. A larger number of flow position differences indicates a higher sensitivity (i.e., a lower limit of detection) for that variant. The target and reference sequencing data sets may be determined by actually sequencing a nucleic acid molecule having the target sequence and/or a nucleic acid molecule having the reference sequence, or the data sets may be expected sequencing data set (for example, as determined in silico).

In one example, the genetic fingerprint of a particular subject or a cancer may be desired, but it is not necessary to detect each and every short genetic variant in the subject's or cancer's genome. Instead, one or more short genetic variant with particularly high sensitivity for a given flow order may be pre-selected. By pre-selecting the sensitive variants, a lower sequencing depth for the test sample can be used to confidently call the variants.

In some embodiments, the method for detecting a target short genetic variant in a test sample may include selecting a target short genetic variant, wherein a target sequencing data set associated with a target sequence comprising the target short genetic variant differs from a reference sequencing data set associated with a reference sequence at two or more flow positions when the target sequencing data set is obtained by sequencing the target sequence using non-terminating nucleotides provided in separate nucleotide flows according to a flow-cycle order, wherein the flow positions corresponds to the nucleotide flows. In some embodiments, the target sequencing data set differs from the reference sequencing data at two or more non-consecutive flow positions. In some embodiments, the target sequencing data set differs from the reference sequencing data at two or more consecutive flow positions. In some embodiments, the target sequencing data set differs from the reference sequencing data at three or more flow positions, which may be consecutive or non-consecutive. In some embodiments, the target sequence differs from the reference sequence at X base positions, and wherein the target sequencing data set differs from the reference sequencing data at (X+2) or more consecutive flow positions. In some embodiments, the target sequencing data set differs from the reference sequencing data set across one or more flow-cycles.

In some embodiments, the method for detecting a target short genetic variant in a test sample may include selecting a target short genetic variant, wherein the target sequencing data set associated with the target sequence comprising the target short genetic variant differs from the reference sequencing data set associated with the reference sequence at two or more flow positions when the target sequencing data set and the reference sequencing data set are obtained by sequencing the target sequence and the reference sequence using non-terminating nucleotides provided in separate nucleotide flows according to a flow-cycle order, wherein the flow positions corresponds to the nucleotide flows. In some embodiments, the target sequencing data set differs from the reference sequencing data at two or more non-consecutive flow positions. In some embodiments, the target sequencing data set differs from the reference sequencing data at two or more consecutive flow positions. In some embodiments, the target sequencing data set differs from the reference sequencing data at three or more flow positions, which may be consecutive or non-consecutive. In some embodiments, the target sequence differs from the reference sequence at X base positions, and wherein the target sequencing data set differs from the reference sequencing data at (X+2) or more consecutive flow positions. In some embodiments, the target sequencing data set differs from the reference sequencing data set across one or more flow-cycles.

Detection of the selected targeted short genetic variant can proceed generally as discussed above. For example, in some embodiments, a test sequencing data set associated with a test nucleic acid molecule having the locus of the target short genetic variant can be obtained. The sequencing data is generated by sequencing the test nucleic acid molecule using non-terminating nucleotides provided in separate nucleotide flows according to the same flow-cycle order used to generate the target and reference sequencing data sets. A match score indicative of a likelihood that the test sequencing data set matches the target sequence having the short genetic variant (or, alternatively or additionally, a match score indicative of a likelihood that the test sequencing data set matches the reference sequence) is determined, and the presence or absence of the target short genetic variant in the test sample can be called using the determined match score.

In some embodiments, the target short genetic variant is detected in the test sample using a plurality of test sequencing data sets, with each test sequencing data set being associated with a different test nucleic acid molecule in a test sample. The analyzed test nucleic acid molecules overlap at the target short genetic variant locus, and the data sets are generated by sequencing the test nucleic acid molecules using the same flow-cycle order used to select the target short genetic variant. A match score indicative of a likelihood that the plurality of test sequencing data sets matches the target sequence having the short genetic variant (or, alternatively or additionally, a match score indicative of a likelihood that the plurality of test sequencing data sets matches the reference sequence) is determined, and the presence or absence of the target short genetic variant in the test sample can be called using the determined match score.

In some embodiments, the flow order or flow-cycle order used to generate the sequencing data is preselected. As discussed herein, the context of the variant in the flow order can affect the signal difference between a variant sequence and a compared (e.g., reference) sequence. To increase the likelihood of detecting a selected target variant, the flow order or flow-cycle order may be pre-selected.

FIG. 3 shows a flow chart of an exemplary method for detecting a short genetic variant in a test sample. At step 302, a target short genetic variant is selected. The target short genetic variant is selected such that target sequencing data associated with a target sequence comprising the target short genetic variant differs from a sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows. At step 304, one or more test sequencing data sets are obtained, for example by sequencing one or more test nucleic acid molecules to obtain the one or more test sequencing data sets, or by receiving the one or more test sequencing data sets. Each of the test sequencing data sets is associated with a test nucleic acid molecule derived from a test sample. For analysis of the selected target short genetic variant, the test nucleic acid molecules at least partially overlaps a locus associated with the target short genetic variant. The sequencing data sets can be determined (or may have previously determined) by sequencing the test nucleic acid molecules using non-terminating nucleotides provided in separate nucleotide flows according to the flow-cycle order, wherein the test sequencing data sets comprise flow signals at the plurality of flow positions. At step 306, for each test nucleic acid molecule associated with a test sequencing data set, a match score is determined. The match score is indicative of a likelihood that the test sequencing data set associated with the nucleic acid molecule matches the target sequence. Alternatively, the match score may be indicative of the likelihood that the test sequencing data set associated with the nucleic acid molecule matches the reference sequence. At step 308, the one or more determined match scores are used to call the presence or absence of the target short genetic variant in the test sample.

In some embodiments, a method for detecting a short genetic variant in a test sample, comprises: (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a method for detecting a short genetic variant in a test sample, comprises: (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) sequencing one or more test nucleic acid molecules using non-terminating nucleotides provided in separate nucleotide flows according to the flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a method for detecting a short genetic variant in a test sample, comprises: (a) preselecting a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a method for detecting a short genetic variant in a test sample, comprises: (a) preselecting a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) sequencing one or more test nucleic acid molecules using non-terminating nucleotides provided in separate nucleotide flows according to the flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a method for detecting a short genetic variant in a test sample, comprises: (a) preselecting a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the preselected flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a method for detecting a short genetic variant in a test sample, comprises: (a) preselecting a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) sequencing one or more test nucleic acid molecules using non-terminating nucleotides provided in separate nucleotide flows according to the preselected flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

Selection of a Target Variant and/or Flow-Cycle Order

Flow cycle orders need not be limited to four base flow cycles (e.g., one each of A, G, C, and T, in any repeated order), and may be an extended flow cycle with more than four base types in a cycle. The extended cycle order may be repeated for the desired number of cycles to extend the sequencing primer. By way of example, in some embodiments, the extended flow order includes 5, 6, 7, 8, 9, 10, 11, 12, 13, 14, 15, 16, 17, 18, 19, 20 or more separate nucleotide flows in the flow cycle order. The cycles can include at least one each of A, G, C, and T, but repeat one or more base types within the cycle before the cycle is repeated.

The extended flow cycle orders can be useful for detecting a greater proportion of small genomic variants (e.g., SNPs) than a flow cycle order with four repeated bases. For example, there are 192 valid configurations of substitution SNPs in the form XYZ XQZ where WY (and Q, X, Y, and Z are each any one of A, C, G, and T). Of these, 168 can produce a new signal (i.e., a new non-zero signal or a new zero signal) in the sequencing data set (e.g., a flowgram). A new zero or non-zero signal combined with a sensitive flow order can produce a signal that is propagated for multiple flow positions (e.g., a flow shift or cycle shift, which may extend more than the length of the cycle), given identical trailing sequences in the variant relative to the reference. It is noted that insertion or deletion of a homopolymer, rather than a homopolymer length change, can result in a signal difference propagation. The remaining 24 variants causes a homopolymer length change at the affected flow position, but such a change does not cause a propagated signal change. Thus, a theoretical maximum of 87.5% of SNPs can result in a new signal that differs from a reference (or candidate) sequence for more than two flow positions. As discussed above, the propagated signal difference increases the likelihood difference between a test sequencing data set and an incorrectly matched candidate sequence. Further, the propagated signal change depends on the flow order spanning the variant.

Sequencing nucleic acid molecules in a test sample that have been randomly fragmented results in a random shift in the flow order context of the variant when the sequencing primer is extended using the flow order. That is, the flow position of the variant may change depending on the start position of the sequenced nucleic acid molecule. Not all flow cycle combinations are able to detect signal changes at more than two flow positions for all 87.5% of SNPs, even if all sequencing start positions in a nucleic acid molecule sequence are utilized. For example, the four-base flow cycle order T-A-C-G can result in a test sequencing data set that differs from a reference sequencing data set at more than two flow positions for 41.7% of SNPs. As further discussed herein, extended flow cycle orders have been designed so that all of the theoretical maximum of SNPs (i.e., 87.5% of possible SNPs, or all SNPs other than those resulting in a homopolymer length change) can give rise to a difference at more than two flow position between the test sequencing data set and the reference sequencing data set, given a high enough sequencing depth (i.e., sampling a sufficiently large number of start positions).

Extended sequencing flow orders may have different efficiencies (i.e., the average number of incorporations per flow when used to sequence a human reference genome). In some embodiments, the flow order has an efficiency of about 0.6 or greater (such as about 0.62 or greater, about 0.64 or greater, about 0.65 or greater, about 0.66 or greater, or about 0.67 or greater). In some embodiments, the flow order has an efficiency of about 0.6 to about 0.7. Examples of flow cycle orders and corresponding estimated efficiencies are shown in Table 2.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 5% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 5% of random sequencing start positions (i.e., "flow phases"). In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 5% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 5% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 10% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 10% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% of SNP permutations for at least 20% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 80% to 87.5% of SNP permutations for at least 20% of random sequencing start positions.

In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 50% to 87.5% (or about 50% to about 80%) of SNP permutations for at least 30% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 60% to 87.5% (or about 60% to about 80%) of SNP permutations for at least 30% of random sequencing start positions. In some embodiments, the extended sequencing flow order is selected to generate signal differences at more than two flow positions between two sequencing data sets (e.g., a test or target sequencing data set and a candidate or reference sequencing data set) associated with nucleic acid molecules differing by a SNP for about 70% to 87.5% (or about 70% to about 80%) of SNP permutations for at least 30% of random sequencing start positions.

In some embodiments, the extended sequencing flow order is any one of the extended sequencing flow orders in Table 2. "Shift sensitivity" refers to the maximum sensitivity to generate signal differences at more than two flow positions between two sequencing data sets (e.g., a test or target sequencing data set and a candidate or reference sequencing data set) over all possible SNP permutations. "Maximum shift sensitivity" refers to refers to the maximum sensitivity to generate signal differences at more than two flow positions between two sequencing data sets (e.g., a test or target sequencing data set and a candidate or reference sequencing data set) over all possible SNP permutations at the highest fraction of flow phases at which that sensitivity is maintained.

TABLE 2

| Flow Cycle Order | Estimated Efficiency | Maximum Shift Sensitivity | Shift Sensitivity @ 5% of Flow Phases | Shift Sensitivity @ 10% of Flow Phases | Shift Sensitivity @ 20% of Flow Phases | Shift Sensitivity @ 30% of Flow Phases |
|---|---|---|---|---|---|---|
| T-C-A-G-A-T-G-C-A-T-G-C-T-A-C-G | 67.5% | 82.3% @ 19% | 82.3% | 82.3% | 75.0% | 66.7% |
| T-C-A-C-G-A-T-G-C-A-T-G-C-T-A-G | 67.5% | 83.3% @ 12% | 83.3% | 83.3% | 72.9% | 62.5% |
| T-C-A-T-G-C-A-T-G-C-T-A-C-G-A-G | 67.3% | 82.3% @ 12% | 82.3% | 82.3% | 72.9% | 67.7% |
| T-C-A-G-T-A-C-G-A-T-G-C-A-T-G-C | 67.3% | 82.3% @ 12% | 82.3% | 82.3% | 75.0% | 63.5% |
| T-C-A-G-T-C-G-A-T-G-A-C-T-A-G-C | 67.2% | 81.3% @ 12% | 81.3% | 81.3% | 74.0% | 69.8% |
| T-C-A-T-C-G-A-C-T-G-A-G-C-T-A-G | 67.2% | 81.3% @ 12% | 81.3% | 81.3% | 74.0% | 69.8% |
| T-C-G-T-A-G-C-T-G-A-C-A-T-G-C-A | 67.2% | 83.3% @ 12% | 83.3% | 83.3% | 75.0% | 67.7% |
| T-C-G-T-A-G-C-A-T-G-C-T-A-C-G-A | 67.0% | 79.2% @ 25% | 79.2% | 79.2% | 79.2% | 75.0% |
| T-C-A-T-G-C-A-G-T-C-G-A-C-T-A-G | 66.9% | 83.3% @ 19% | 83.3% | 83.3% | 75.0% | 68.8% |
| T-C-A-T-G-C-A-T-C-G-T-A-C-G-A-G-C-T-G-C-A-T-G-A-C-T-A-G | 66.7% | 86.5% @ 7% | 86.5% | 85.4% | 85.4% | 69.8% |
| T-C-G-A-C-T-G-T-A-G-C-T-A-G-C-A | 66.7% | 82.3% @ 19% | 82.3% | 82.3% | 75.0% | 66.7% |
| T-C-A-C-G-A-T-G-C-T-A-G-C-T-A-G | 66.5% | 82.3% @ 12% | 82.3% | 82.3% | 75.0% | 66.7% |
| T-C-A-G-T-A-C-G-A-T-G-C-T-A-C-G | 66.4% | 83.3% @ 19% | 83.3% | 83.3% | 75.0% | 68.8% |
| T-C-G-A-C-T-A-G-C-A-T-G-C-A-T-G | 66.0% | 81.3% @ 12% | 81.3% | 81.3% | 70.8% | 62.5% |
| T-A-C-G | 66.0% | 41.7% @ 100% | 41.7% | 41.7% | 41.7% | 41.7% |
| T-C-A-G-C-T-G-A-C-T-A-G-T-C-A-T-G-A-C-T-A-G-C-G-A-T-C-G | 65.7% | 87.5% @ 11% | 87.5% | 87.5% | 82.3% | 75.0% |
| T-C-T-A-G-C-A-T-G-A-C-T-G-A-C-G | 65.7% | 83.3% @ 12% | 83.3% | 83.3% | 71.9% | 63.5% |
| T-C-G-A-C-T-A-T-G-C-A-T-G-C-A-G | 65.5% | 81.3% @ 19% | 81.3% | 81.3% | 71.9% | 63.5% |
| T-C-G-A-C-T-G-C-A-T-C-G-A-T-G-C-A-G-T-A-C-T-A-G | 65.4% | 87.5% @ 12% | 87.5% | 87.5% | 82.3% | 74.0% |
| T-C-A-C-T-G-A-C-G-T-A-G-C-T-A-T-G-C-A-T-C-G-A-G | 65.3% | 84.4% @ 17% | 84.4% | 84.4% | 83.3% | 76.0% |
| T-C-A-T-G-C-T-A-G-C-T-A-G-T-A-C-G-A-C-T-G-A-G-C-A-T-C-G | 65.2% | 86.5% @ 11% | 86.5% | 86.5% | 82.3% | 78.1% |
| T-C-G-A-T-G-C-A-T-C-G-T-A-C-T-A-G-C-A-G-T-G-A-C | 65.2% | 87.5% @ 8% | 87.5% | 86.5% | 84.4% | 71.9% |
| T-C-A-T-G-A-G-C-T-A-G-C-A-T-C-G-T-A-C-T-G-A-C-G | 65.2% | 87.5% @ 8% | 87.5% | 86.5% | 81.3% | 70.8% |
| T-C-A-G-C-A-T-G-T-A-C-T-G-A-T-G-C-A-T-C-G-A-G-C-T-A-C-G | 65.0% | 87.5% @ 11% | 87.5% | 87.5% | 82.3% | 77.1% |
| T-C-A-G-T-A-C-T-A-G-C-A-T-G-C-G-A-T-C-G-T-A-G-C-T-A-C-G | 65.0% | 86.5% @ 11% | 86.5% | 86.5% | 78.1% | 74.0% |

TABLE 2-continued

| Flow Cycle Order | Estimated Efficiency | Maximum Shift Sensitivity | Shift Sensitivity @ 5% of Flow Phases | Shift Sensitivity @ 10% of Flow Phases | Shift Sensitivity @ 20% of Flow Phases | Shift Sensitivity @ 30% of Flow Phases |
|---|---|---|---|---|---|---|
| T-C-A-C-G-T-A-G-C-T-A-T-G-C-T-G-A-C-T-G-A-C-A-T-G-A-C-T-A-G-C-G | 64.6% | 85.4% @ 9% | 85.4% | 84.4% | 76.0% | 61.5% |
| T-C-A-G-C-T-A-T-G-A-C-T-G-A-G-C-A-T-C-G-T-A-C-G | 64.5% | 85.4% @ 12% | 85.4% | 85.4% | 77.1% | 74.0% |
| T-C-A-G-C-T-A-C-T-G-C-A-T-G-A-C-G-T-A-C-G-T-A-G-T-C-G-A | 64.5% | 87% @ 14% | 87.5% | 87.5% | 83.3% | 70.8% |
| T-C-A-G-A-C-T-A-G-C-G-A-T-G-C-A-T-G-T-C-T-A-G-T-C-A-C-G | 64.5% | 86.5% @ 11% | 86.5% | 86.5% | 83.3% | 62.5% |
| T-C-A-T-C-G-A-C-T-G-C-G-A-T-G-C-T-A-G-T-A-C-A-G | 64.4% | 85.4% @ 17% | 85.4% | 85.4% | 83.3% | 72.9% |
| T-C-A-C-G-T-A-C-T-G-A-C-A-T-G-C-A-T-G-C-T-A-G-T-A-G-C-G-A-T-C-G | 64.4% | 85.4% @ 9% | 85.4% | 85.4% | 83.3% | 72.9% |
| T-C-A-G-T-G-C-T-A-C-G-T-C-A-C-G-A-T-C-A-G-A-T-G-C-T-A-G | 64.4% | 86.5% @ 11% | 86.5% | 86.5% | 71.9% | 67.7% |
| T-C-A-G-C-G-A-T-G-A-C-T-A-G-C-T-A-C-G-T-C-A-T-G | 64.4% | 85.4% @ 17% | 85.4% | 85.4% | 84.4% | 66.7% |
| T-C-A-T-G-C-T-A-C-G-A-G | 64.4% | 81.3% @ 17% | 81.3% | 81.3% | 80.2% | 66.7% |
| T-C-A-T-G-A-C-G-T-A-C-G-A-C-T-C-A-T-G-C-A-G-T-G-C-T-A-G | 64.3% | 85.4% @ 11% | 85.4% | 85.4% | 82.3% | 75.0% |
| T-C-A-G-T-C-G-A-T-G-C-T-A-C-T-G-C-A-T-A-C-G-T-C-G-A-T-G-A-C-A-G | 64.3% | 87.5% @ 9% | 87.5% | 86.5% | 83.3% | 74.0% |
| T-C-G-A-T-G-C-T-A-C-A-G | 64.3% | 81.3% @ 17% | 81.3% | 81.3% | 80.2% | 66.7% |
| T-C-A-G-T-C-G-A-C-A-T-G-C-A-T-C-G-A-T-A-C-G-T-G-C-T-A-G-C-T-A-G | 64.2% | 87.5% @ 9% | 87.5% | 86.5% | 79.2% | 70.8% |

In some embodiments, a method of sequencing a nucleic acid molecule, comprises (a) hybridizing the nucleic acid molecule to a primer to form a hybridized template; (b) extending the primer using labeled, non-terminating nucleotides provided in separate nucleotide flows according to a repeated flow-cycle order comprising five or more separate nucleotide flows; and (c) detecting a signal from an incorporated labeled nucleotide or an absence of a signal as the primer is extended by the nucleotide flows. In some embodiments, the flow-cycle order induces a signal change at more than two flow positions for 50% or more of possible SNP permutations at 5% of random sequencing start positions. In some embodiments, the induced signal change is a change in signal intensity, or a new substantially zero (or new zero) or a new substantially non-zero (or new non-zero) signal. In some embodiments, the induced signal change is a new substantially zero (or new zero) or a new substantially non-zero (or new non-zero) signal. In some embodiments, the flow-cycle order has an efficiency of 0.6 or more base incorporations per flow. In some embodiments, the flow-cycle is any one of the flow-cycle orders listed in Table 2.

Re-Sequencing with Different Flow Orders

As the sensitivity of a short genetic variant detected depends on the flow cycle order used to sequencing the nucleic acid molecule, the methods described herein may be adapted to analyze a test nucleic acid molecules (or a plurality of nucleic acid molecules with an overlapping locus) sequenced using two or more different flow cycle orders. The match score can be determined based on the match of the two or more different sequencing data sets (resulting from the different flow cycle orders) to one or more candidate sequences. The presence or absence of the variant may be called and/or the candidate sequence selected based on the match score as discussed above.

The method can include obtaining a first test sequencing data set associated with a test nucleic acid molecule derived from a test sample sequenced using a first flow-cycle order, and a second test sequencing data set associated with the same test nucleic acid molecule sequenced using a second flow-cycle order. For example, the test nucleic acid molecule may be sequenced by providing non-terminating nucleic acid molecules in separate nucleotide flows according to the first flow-cycle order, extending a sequencing primer, and detecting the presence or absence of nucleotide incorporation into the sequencing primer after each nucleotide flow to generate the first test sequencing data set; removing the extended sequencing primer; and sequencing the same test nucleic acid molecule by providing the non-terminating nucleotides in separate nucleotide flows according to the second flow-cycle order, extending a sequencing primer, and detecting the presence or absence of nucleotide incorporation into the sequencing primer after each nucleotide flow to generate the second test sequencing data set.

Figures 4A, 4B:
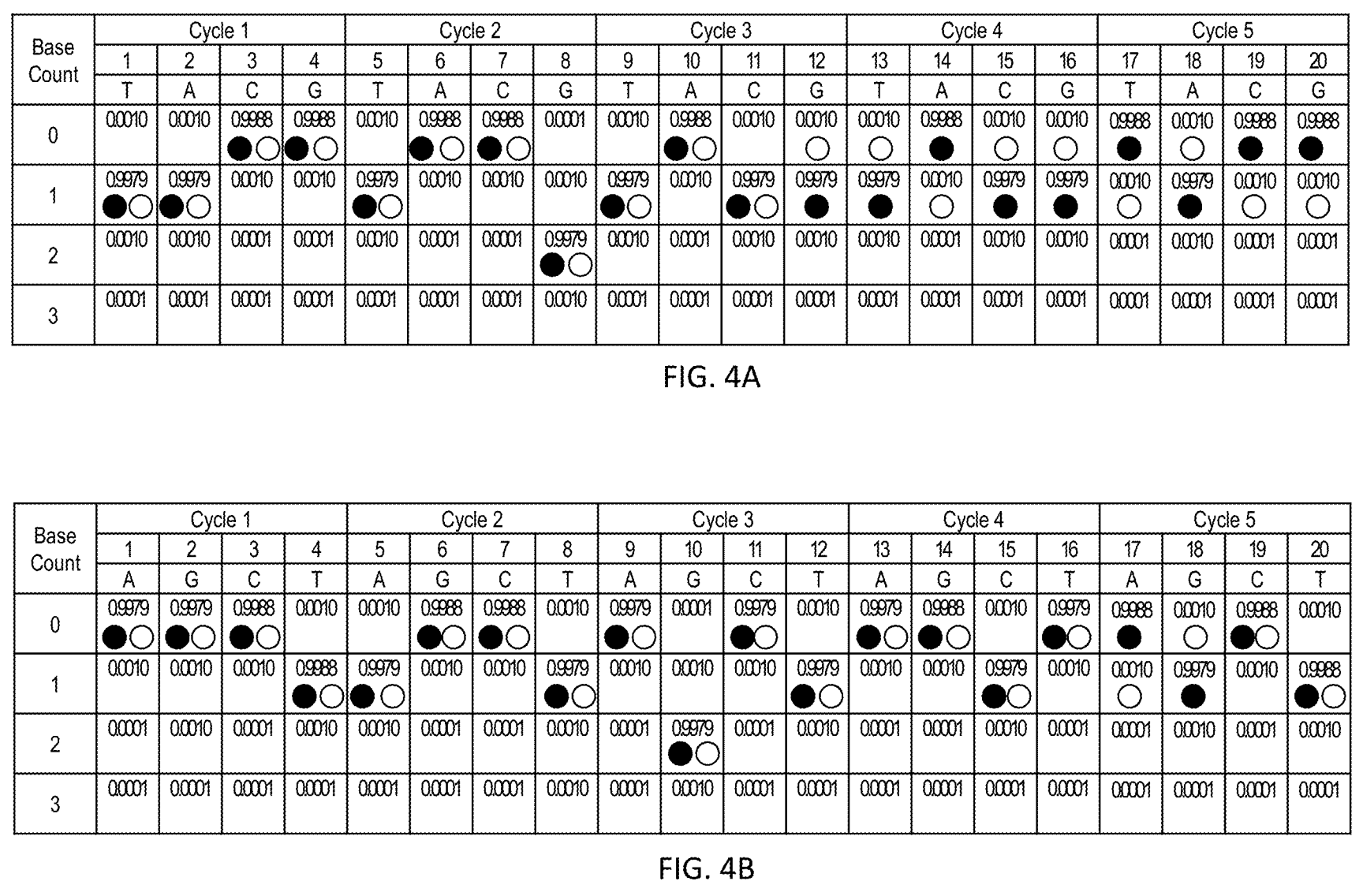

Because the nucleic acid molecule is sequenced using different flow-cycle orders, the sequencing data sets differ. FIG. 4A and FIG. 4B show exemplary sequencing data sets for a nucleic acid molecule having an extended primer sequence of TATGGTCGTCGA (SEQ ID NO: 1) determined using a first flow-cycle order (T-A-C-G) (FIG. 4A) and a second flow-cycle order (A-G-C-T) (FIG. 4B). As seen, the sequencing data sets in FIG. 4A and FIG. 4B differ due to differences in the flow-cycle order even though the nucleic acid molecule sequence does not change. Within the sequencing data set, statistical parameters at each flow position that corresponds with a base count of a first candidate extended primer sequence TATGGTCGTCGA (SEQ ID NO: 1) (closed circles) and a second candidate extended primer sequence TATGGTCATCGA (SEQ ID NO: 2) (open circles) can be selected. FIG. 4A and FIG. 4B demonstrate the significant change the flow cycle order has on variant detection sensitivity. For example, the difference between the first candidate sequence and the second candidate sequence using the first flow cycle order is apparent at flow positions 12-20 (FIG. 4A), whereas the difference between the first candidate sequence and the second candidate sequence using the first flow cycle order is apparent only at positions 17 and 18 (FIG. 4B).

A match score indicative of a likelihood that the first sequencing data set and the second sequencing data set match one or more candidate sequence (e.g., a target sequence having a preselected target short genetic variant, a reference sequence having a sequence without the preselected target short genetic variant, or other possible candidate sequence (such as a haplotype)) can be determine, and the presence or absence of the target short genetic variant can be called or a candidate sequence selected.

As discussed herein, this process may be used when sequencing a plurality of different test nucleic acid molecules that overlap at a common locus. For example, a plurality of first test sequencing data sets, with each test sequencing data set associated with a test nucleic acid molecule sequenced using a first flow cycle order, can be obtained, and a plurality of second test sequencing data sets, with each test sequencing data set associated with the same nucleic acid molecules sequenced using a second flow cycle order, can be obtained. The first flow cycle order and the second flow cycle order are different. A match score indicative of a likelihood that the plurality of first sequencing data sets and the plurality of second sequencing data sets match one or more candidate sequence (e.g., a target sequence having a preselected target short genetic variant, a reference sequence having a sequence without the preselected target short genetic variant, or other possible candidate sequence (such as a haplotype)) can be determine, and the presence or absence of the target short genetic variant can be called or a candidate sequence selected.

Figure 5:
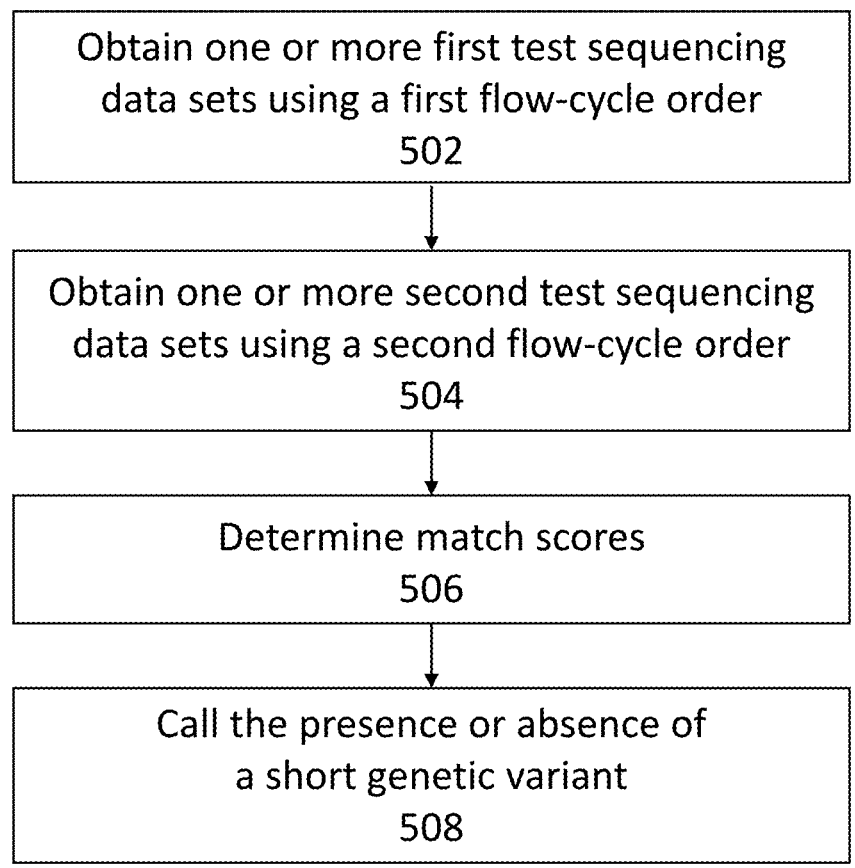
FIG. 5 shows another exemplary method for detecting the presence or absence of a short genetic variant in a test sample.

FIG. 5 shows an exemplary method for detecting the presence or absence of a short genetic variant in a test sample. At step 502, one or more first test sequencing data sets are obtained. The one or more first test sequencing data sets may be obtained, for example, by receiving the one or more first test sequencing data sets, or by sequencing one or more nucleic acid molecules. Each of the first test sequencing data sets are associated with a different nucleic acid molecule derived from the test sample. The first sequencing data sets are determined by sequencing the one or more test nucleic acid molecules using non-terminating nucleotides provided in separate nucleotide flows according to a first flow-cycle order. The resulting one or more first test sequencing data sets each comprise flow signals at flow positions corresponding to the nucleotide flows. At step 504, one or more second test sequencing data sets are obtained. The one or more second test sequencing data sets may be obtained, for example, by receiving the one or more second test sequencing data sets, or by sequencing one or more nucleic acid molecules. Each of the second test sequencing data sets are associated with the same nucleic acid molecule as a first test sequencing data set. That is, a nucleic acid molecule is associated with both a first sequencing data set and a second sequencing data set. The second sequencing data sets are determined by sequencing the one or more test nucleic acid molecules using non-terminating nucleotides provided in separate nucleotide flows according to a second flow-cycle order that is different from the first flow-cycle order. The resulting one or more second test sequencing data sets each comprise flow signals at flow positions corresponding to the nucleotide flows. At step 506, for each first sequencing data set and second sequencing data set, a match score is determined. The match score is indicative that the first test sequencing data set, the sequencing data set or both matches a candidate sequence from one or more candidate sequences. At step 508, the presence or absence of a short genetic variant in the test sample is called using the determined match scores.

Figure 6:
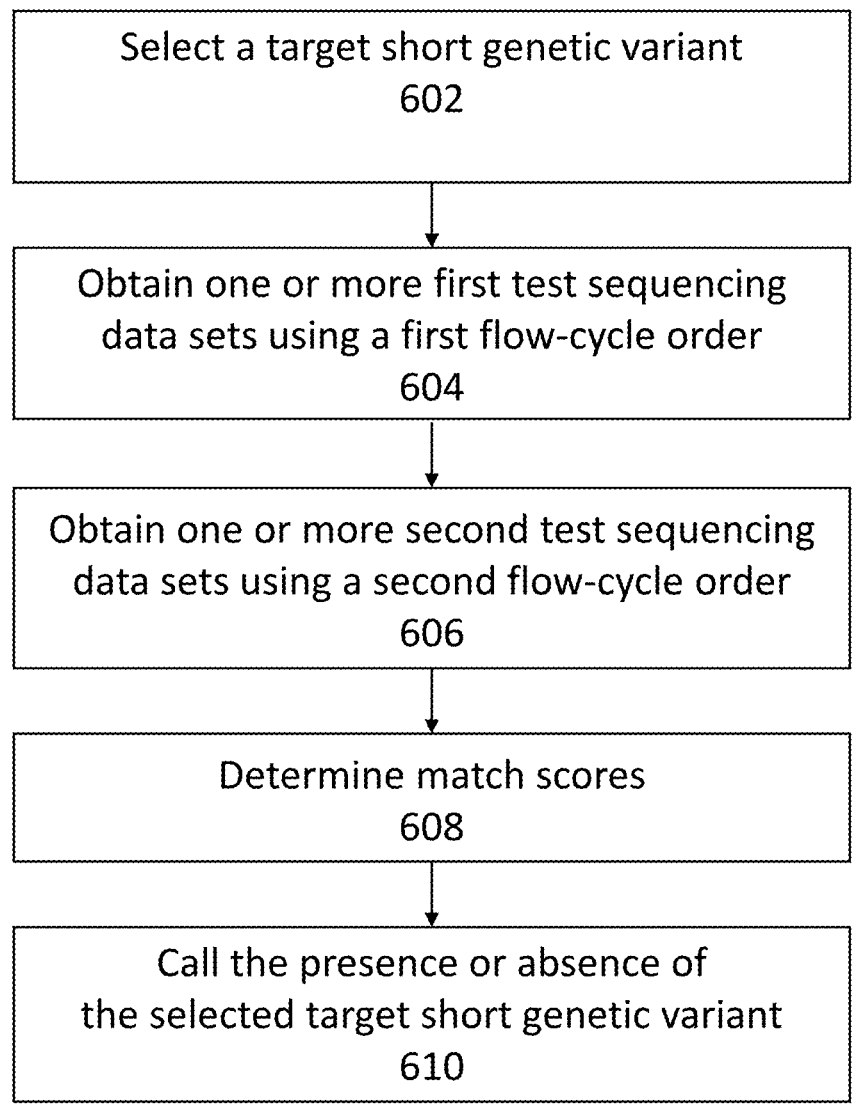
FIG. 6 shows another exemplary method for detecting the presence or absence of a short genetic variant in a test sample.

FIG. 6 shows another exemplary method for detecting the presence or absence of a short genetic variant in a test sample. At step 602, a target short genetic variant is selected. The target short genetic variant is selected such that target sequencing data associated with a target sequence comprising the target short genetic variant differs from a sequencing data set associated with a reference sequence at more than two flow positions when the target sequencing data set and the reference sequencing data set are obtained by sequencing the target sequence using non-terminating nucleotides provided in separate nucleotide flows according to a first flow-cycle order or a second flow-cycle order, or both, wherein the first flow-cycle order and the second flow-cycle order are different, and wherein the flow positions correspond to the nucleotide flows. At step 604, one or more first test sequencing data sets are obtained. The one or more first test sequencing data sets may be obtained, for example, by receiving the one or more first test sequencing data sets, or by sequencing one or more nucleic acid molecules. Each of the first test sequencing data sets are associated with a different nucleic acid molecule derived from the test sample. The first sequencing data sets are determined by sequencing the one or more test nucleic acid molecules using non-terminating nucleotides provided in separate nucleotide flows according to a first flow-cycle order. The resulting one or more first test sequencing data sets each comprise flow signals at flow positions corresponding to the nucleotide flows. At step 606, one or more second test sequencing data sets are obtained. The one or more second test sequencing data sets may be obtained, for example, by receiving the one or more second test sequencing data sets, or by sequencing one or more nucleic acid molecules. Each of the second test sequencing data sets are associated with the same nucleic acid molecule as a first test sequencing data set. That is, a nucleic acid molecule is associated with both a first sequencing data set and a second sequencing data set. The second sequencing data sets are determined by sequencing the one or more test nucleic acid molecules using non-terminating nucleotides provided in separate nucleotide flows according to a second flow-cycle order that is different from the first flow-cycle order. The resulting one or more second test sequencing data sets each comprise flow signals at flow positions corresponding to the nucleotide flows. At step 608, for each first sequencing data set and second sequencing data set, a match score is determined. The match score is indicative that the first test sequencing data set, the sequencing data set or both matches a candidate sequence from one or more candidate sequences (which may include, for example, the reference sequence). At step 610, the presence or absence of a short genetic variant in the test sample is called using the determined match scores.

In some embodiments, a method for detecting the presence or absence of a short genetic variant in a test sample comprises: (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

In some embodiments, a method for detecting the presence or absence of a short genetic variant in a test sample comprises: (a) sequencing one or more test nucleic acid molecules derived from the test sample using non-terminating nucleotides provided in separate nucleotide flows according to a first flow-cycle order to obtain one or more first test sequencing data sets comprising flow signals at flow positions corresponding to the nucleotide flows, each first test sequencing data set associated with a different test nucleic acid molecule; (b) sequencing the same one or more test nucleic acid molecules derived from the test sample using non-terminating nucleotides provided in separate nucleotide flows according to a second flow-cycle order, wherein the second flow-cycle order is different from the first flow-cycle order, to obtain one or more second test sequencing data sets comprising flow signals at flow positions corresponding to the nucleotide flows, each second test sequencing data set associated with the same test nucleic acid molecule as one of the first test sequencing data sets; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

In some embodiments, a method for detecting the presence or absence of a short genetic variant in a test sample comprises: (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (d) selecting a candidate sequence from the two or more different candidate sequences, wherein the selected candidate sequence has the highest likelihood match with the first test sequencing data set, the second test sequencing data set, or both; and (e) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, a method for detecting the presence or absence of a short genetic variant in a test sample comprises: (a) sequencing one or more test nucleic acid molecules derived from the test sample using non-terminating nucleotides provided in separate nucleotide flows according to a first flow-cycle order to obtain one or more first test sequencing data sets comprising flow signals at flow positions corresponding to the nucleotide flows, each first test sequencing data set associated with a different test nucleic acid molecule; (b) sequencing the same one or more test nucleic acid molecules derived from the test sample using non-terminating nucleotides provided in separate nucleotide flows according to a second flow-cycle order, wherein the second flow-cycle order is different from the first flow-cycle order, to obtain one or more second test sequencing data sets comprising flow signals at flow positions corresponding to the nucleotide flows, each second test sequencing data set associated with the same test nucleic acid molecule as one of the first test sequencing data sets; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (d) selecting a candidate sequence from the two or more different candidate sequences, wherein the selected candidate sequence has the highest likelihood match with the first test sequencing data set, the second test sequencing data set, or both; and (e) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, a method for detecting the presence or absence of a short genetic variant in a test sample comprises: (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to the first flow-cycle order, and wherein the one or more first test sequencing data sets comprise flow signals at flow positions corresponding to the nucleotide flows; (c) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to the second flow-cycle order, wherein the test sequencing data set comprises flow signals at flow positions corresponding to the nucleotide flows; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (e) calling, using the determined match scores, the presence or absence of a short genetic variant in the test sample.

In some embodiments, a method for detecting the presence or absence of a short genetic variant in a test sample comprises: (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) sequencing one or more test nucleic acid molecules derived from the test sample using non-terminating nucleotides provided in separate nucleotide flows according to the first flow-cycle order to obtain one or more first test sequencing data sets comprising flow signals at flow positions corresponding to the nucleotide flows, each first test sequencing data set associated with a different test nucleic acid molecule; (c) sequencing the same one or more test nucleic acid molecules derived from the test sample using non-terminating nucleotides provided in separate nucleotide flows according to the second flow-cycle order to obtain one or more second test sequencing data sets comprising flow signals at flow positions corresponding to the nucleotide flows, each second test sequencing data set associated with the same test nucleic acid molecule as one of the first test sequencing data sets; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (e) calling, using the determined match scores, the presence or absence of a short genetic variant in the test sample.

In some embodiments, a method for detecting the presence or absence of a short genetic variant in a test sample comprises: (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to the first flow-cycle order, and wherein the one or more first test sequencing data sets comprise flow signals at flow positions corresponding to the nucleotide flows; (c) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to the second flow-cycle order, wherein the test sequencing data set comprises flow signals at flow positions corresponding to the nucleotide flows; (d) determining, for each first sequencing data set and second sequencing data set, a match score for one or more candidate sequences (which may include the reference sequence), wherein the match score is indicative of a likelihood that the first test sequencing data set, the second test sequencing data set, or both, matches a candidate sequence from the one or more candidate sequences; (e) selecting a candidate sequence from the two or more different candidate sequences, wherein the selected candidate sequence has the highest likelihood match with the first test sequencing data set, the second test sequencing data set, or both; and (f) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, a method for detecting the presence or absence of a short genetic variant in a test sample comprises: (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) sequencing one or more test nucleic acid molecules derived from the test sample using non-terminating nucleotides provided in separate nucleotide flows according to the first flow-cycle order to obtain one or more first test sequencing data sets comprising flow signals at flow positions corresponding to the nucleotide flows, each first test sequencing data set associated with a different test nucleic acid molecule; (c) sequencing the same one or more test nucleic acid molecules derived from the test sample using non-terminating nucleotides provided in separate nucleotide flows according to the second flow-cycle order to obtain one or more second test sequencing data sets comprising flow signals at flow positions corresponding to the nucleotide flows, each second test sequencing data set associated with the same test nucleic acid molecule as one of the first test sequencing data sets; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (e) selecting a candidate sequence from the two or more different candidate sequences (which may include the reference sequence), wherein the selected candidate sequence has the highest likelihood match with the first test sequencing data set, the second test sequencing data set, or both; and (f) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

Systems, Devices, and Reports

The operations described above, including those described with reference to the Figures, are optionally implemented by one or more components depicted in FIG. 7. It would be clear to a person of ordinary skill in the art how other processes, for example, combinations or subcombinations of all or part of the operations described above, may be implemented based on the components depicted in FIG. 7. It would also be clear to a person having ordinary skill in the art how the methods, techniques, systems, and devices described herein may be combined with one another, in whole or in part, whether or not those methods, techniques, systems, and/or devices are implemented by and/or provided by the components depicted in FIG. 7.

Figure 7:
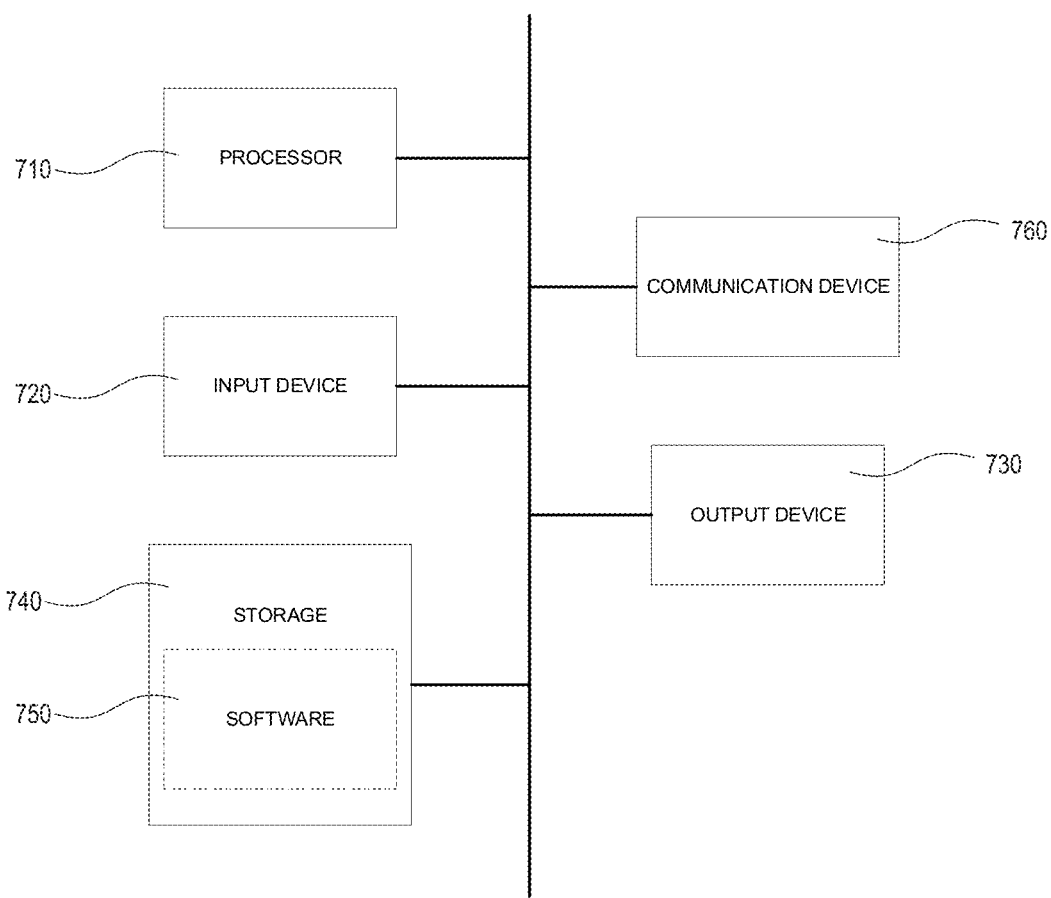
FIG. 7 illustrates an example of a computing device in accordance with one embodiment, which may be used to implement the methods described herein.

FIG. 7 illustrates an example of a computing device in accordance with one embodiment. Device 700 can be a host computer connected to a network. Device 700 can be a client computer or a server. As shown in FIG. 7, device 700 can be any suitable type of microprocessor-based device, such as a personal computer, workstation, server, or handheld computing device (portable electronic device) such as a phone or tablet. The device can include, for example, one or more of processor 710, input device 720, output device 730, storage 740, and communication device 760. Input device 720 and output device 730 can generally correspond to those described above, and can either be connectable or integrated with the computer.

Input device 720 can be any suitable device that provides input, such as a touch screen, keyboard or keypad, mouse, or voice-recognition device. Output device 730 can be any suitable device that provides output, such as a touch screen, haptics device, or speaker.

Storage 740 can be any suitable device that provides storage, such as an electrical, magnetic or optical memory including a RAM, cache, hard drive, or removable storage disk. Communication device 760 can include any suitable device capable of transmitting and receiving signals over a network, such as a network interface chip or device. The components of the computer can be connected in any suitable manner, such as via a physical bus or wirelessly.

Software 750, which can be stored in storage 740 and executed by processor 710, can include, for example, the programming that embodies the functionality of the present disclosure (e.g., as embodied in the devices as described above).

Software 750 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 740, that can contain or store programming for use by or in connection with an instruction execution system, apparatus, or device.

Software 750 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 700 can implement any operating system suitable for operating on the network. Software 750 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The methods described herein optionally further include reporting information determined using the analytical methods and/or generating a report containing the information determined suing the analytical methods. For example, in some embodiments, the method further includes reporting or generating a report containing related to the identification of a variant in a polynucleotide derived from a subject (e.g., within a subject's genome). Reported information or information within the report may be associated with, for example, a locus of a coupled sequencing read pair mapped to a reference sequence, a detected variant (such as a detected structural variant or detected SNP), one or more assembled consensus sequences and/or the a validation statistic for the one or more assembled consensus sequences. The report may be distributed to or the information may be reported to a recipient, for example a clinician, the subject, or a researcher.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) sequencing one or more test nucleic acid molecules using non-terminating nucleotides provided in separate nucleotide flows according to the flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) preselecting a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) preselecting a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) sequencing one or more test nucleic acid molecules using non-terminating nucleotides provided in separate nucleotide flows according to the flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) preselecting a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) obtaining one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the preselected flow-cycle order, and wherein the test sequencing data set comprises flow signals at the plurality of flow positions; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) preselecting a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) sequencing one or more test nucleic acid molecules using non-terminating nucleotides provided in separate nucleotide flows according to the preselected flow-cycle order to obtain one or more test sequencing data sets comprising flow signals at a plurality of flow positions, each test sequencing data set associated with a test nucleic acid molecule, and each test nucleic acid molecule at least partially overlapping a locus associated with the target short genetic variant and derived from the test sample; (c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, there is a system comprising one or more processors; and a non-transitory computer-readable medium that stores one or more programs comprising instructions for (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

In some embodiments, there is a system comprising one or more processors; and a non-transitory computer-readable medium that stores one or more programs comprising instructions for (a) sequencing one or more test nucleic acid molecules derived from the test sample using non-terminating nucleotides provided in separate nucleotide flows according to a first flow-cycle order to obtain one or more first test sequencing data sets comprising flow signals at flow positions corresponding to the nucleotide flows, each first test sequencing data set associated with a different test nucleic acid molecule; (b) sequencing the same one or more test nucleic acid molecules derived from the test sample using non-terminating nucleotides provided in separate nucleotide flows according to a second flow-cycle order, wherein the second flow-cycle order is different from the first flow-cycle order, to obtain one or more second test sequencing data sets comprising flow signals at flow positions corresponding to the nucleotide flows, each second test sequencing data set associated with the same test nucleic acid molecule as one of the first test sequencing data sets; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (d) calling, using the determined match scores, the presence or absence of a short genetic variant in the test sample.

In some embodiments, there is a system comprising one or more processors; and a non-transitory computer-readable medium that stores one or more programs comprising instructions for (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows; (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (d) selecting a candidate sequence from the two or more different candidate sequences, wherein the selected candidate sequence has the highest likelihood match with the first test sequencing data set, the second test sequencing data set, or both; and (e) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, there is a system comprising one or more processors; and a non-transitory computer-readable medium that stores one or more programs comprising instructions for (a) sequencing one or more test nucleic acid molecules derived from the test sample using non-terminating nucleotides provided in separate nucleotide flows according to a first flow-cycle order to obtain one or more first test sequencing data sets comprising flow signals at flow positions corresponding to the nucleotide flows, each first test sequencing data set associated with a different test nucleic acid molecule; (b) sequencing the same one or more test nucleic acid molecules derived from the test sample using non-terminating nucleotides provided in separate nucleotide flows according to a second flow-cycle order, wherein the second flow-cycle order is different from the first flow-cycle order, to obtain one or more second test sequencing data sets comprising flow signals at flow positions corresponding to the nucleotide flows, each second test sequencing data set associated with the same test nucleic acid molecule as one of the first test sequencing data sets; (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (d) selecting a candidate sequence from the two or more different candidate sequences, wherein the selected candidate sequence has the highest likelihood match with the first test sequencing data set, the second test sequencing data set, or both; and (e) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to the first flow-cycle order, and wherein the one or more first test sequencing data sets comprise flow signals at flow positions corresponding to the nucleotide flows; (c) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to the second flow-cycle order, wherein the test sequencing data set comprises flow signals at flow positions corresponding to the nucleotide flows; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (e) calling, using the determined match scores, the presence or absence of a short genetic variant in the test sample.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) sequencing one or more test nucleic acid molecules derived from the test sample using non-terminating nucleotides provided in separate nucleotide flows according to the first flow-cycle order to obtain one or more first test sequencing data sets comprising flow signals at flow positions corresponding to the nucleotide flows, each first test sequencing data set associated with a different test nucleic acid molecule; (c) sequencing the same one or more test nucleic acid molecules derived from the test sample using non-terminating nucleotides provided in separate nucleotide flows according to the second flow-cycle order to obtain one or more second test sequencing data sets comprising flow signals at flow positions corresponding to the nucleotide flows, each second test sequencing data set associated with the same test nucleic acid molecule as one of the first test sequencing data sets; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and (e) calling, using the determined match scores, the presence or absence of a short genetic variant in the test sample.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to the first flow-cycle order, and wherein the one or more first test sequencing data sets comprise flow signals at flow positions corresponding to the nucleotide flows; (c) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to the second flow-cycle order, wherein the test sequencing data set comprises flow signals at flow positions corresponding to the nucleotide flows; (d) determining, for each first sequencing data set and second sequencing data set, a match score for one or more candidate sequences (which may include the reference sequence), wherein the match score is indicative of a likelihood that the first test sequencing data set, the second test sequencing data set, or both, matches a candidate sequence from the one or more candidate sequences; (e) selecting a candidate sequence from the two or more different candidate sequences, wherein the selected candidate sequence has the highest likelihood match with the first test sequencing data set, the second test sequencing data set, or both; and (f) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, there is a system comprising one or more processors; and a non-transitory computer-readable medium that stores one or more programs comprising instructions for (a) selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to a first flow-cycle order or a second flow cycle order, wherein the first flow-cycle order is different from the second flow-cycle order, and wherein the flow positions corresponds to the nucleotide flows; (b) sequencing one or more test nucleic acid molecules derived from the test sample using non-terminating nucleotides provided in separate nucleotide flows according to the first flow-cycle order to obtain one or more first test sequencing data sets comprising flow signals at flow positions corresponding to the nucleotide flows, each first test sequencing data set associated with a different test nucleic acid molecule; (c) sequencing the same one or more test nucleic acid molecules derived from the test sample using non-terminating nucleotides provided in separate nucleotide flows according to the second flow-cycle order to obtain one or more second test sequencing data sets comprising flow signals at flow positions corresponding to the nucleotide flows, each second test sequencing data set associated with the same test nucleic acid molecule as one of the first test sequencing data sets; (d) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; (e) selecting a candidate sequence from the two or more different candidate sequences (which may include the reference sequence), wherein the selected candidate sequence has the highest likelihood match with the first test sequencing data set, the second test sequencing data set, or both; and (f) calling, using the selected candidate sequence, the presence or absence of the short genetic variant in the test sample. In some embodiments, at least one non-selected candidate sequence from the two or more different candidate sequences differs from the selected candidate sequence at two or more (or three or more, or across one or more flow-cycles) flow positions (which may be consecutive or non-consecutive) according to the first flow-cycle order and/or the second flow-cycle order.

In some embodiments, the methods described herein are computer-implemented methods, which may be performed using one or more of the components illustrated in FIG. 7. For example, in some embodiments, a computer-implemented method for detecting a short genetic variant in a test sample, comprises: (a) selecting, using one or more processors, a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) receiving, at the one or more processors, one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, using the one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, using the one or more processors and the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a computer-implemented method for detecting a short genetic variant in a test sample, comprises: (a) preselecting, using one or more processors, a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) receiving, at the one or more processors, one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, at the one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, at the one or more processors and using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a computer-implemented method for detecting a short genetic variant in a test sample, comprises: (a) preselecting, using one or more processors, a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) receiving, at the one or more processors, one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the preselected flow-cycle order, and wherein the test sequencing data set comprises flow signals at the plurality of flow positions; (c) determining, at the one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, at the one or more processors and using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a computer-implemented method for detecting a short genetic variant in a test sample comprises (a) selecting, at one or more processors, a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) receiving, at the one or more processors, one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, at the one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, at the one or more processors and using the one or more determined match scores, the presence or absence of the target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a computer-implemented method for detecting a short genetic variant in a test sample, comprises: (a) preselecting, at one or more processors, a target short genetic variant, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows; (b) receiving, at one or more processors, one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions; (c) determining, at one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, at one or more processors and using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

In some embodiments, a computer-implemented method for detecting a short genetic variant in a test sample, comprises: (a) preselecting, at one or more processors, a target short genetic variant and a flow-cycle order, wherein a target sequencing data set associated with a target sequence comprising the preselected target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to the preselected flow-cycle order, wherein the flow positions correspond to the nucleotide flows; (b) receiving, at the one or more processors, one or more test sequencing data sets, each test sequencing data set associated with a test nucleic acid molecule, each test nucleic acid molecule at least partially overlapping a locus associated with the preselected target short genetic variant and derived from the test sample, wherein the one or more test sequencing data sets were determined by sequencing the test nucleic acid molecule using non-terminating nucleotides provided in separate nucleotide flows according to the preselected flow-cycle order, and wherein the test sequencing data set comprises flow signals at the plurality of flow positions; (c) determining, at the one or more processors, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and (d) calling, at the one or more processors and using the one or more determined match scores, the presence or absence of the preselected target short genetic variant in the test sample. In some embodiments, the method further comprises generating a personalized biomarker panel for a subject associated with the test sample, the biomarker panel comprising the target short genetic variant. In some embodiments, the target sequencing data set differs from the reference sequencing data set at more than two flow positions (e.g., more than two consecutive flow positions or more than two non-consecutive flow positions). In some embodiments, the target sequencing data set differs from the reference sequencing data set across one or more flow-cycles.

EXEMPLARY EMBODIMENTS

The following embodiments are exemplary and are not intended to limit the scope of the claimed invention.

Embodiment 1. A method for detecting a short genetic variant in a test sample, comprising:
(a) selecting a target short genetic variant, wherein a target sequencing data set associated with a target sequence comprising the target short genetic variant differs from a reference sequencing data set associated with a reference sequence at more than two flow positions when the target sequencing data set and the reference sequencing data set are obtained by sequencing the target sequence using non-terminating nucleotides provided in separate nucleotide flows according to a flow-cycle order, wherein the flow positions correspond to the nucleotide flows;
(b) obtaining one or more test sequencing data sets, each test sequencing data set associated with a test nucleic acid molecule, each test nucleic acid molecule at least partially overlapping a locus associated with the target short genetic variant and derived from the test sample, wherein the one or more test sequencing data sets were determined by sequencing the test nucleic acid molecule using non-terminating nucleotides provided in separate nucleotide flows according to the flow-cycle order, and wherein the test sequencing data set comprises flow signals at the plurality of flow positions;
(c) determining, for each test nucleic acid molecule associated with a test sequencing data set, a match score indicative of a likelihood that the test sequencing data set associated with the nucleic acid molecule matches the target sequence, or a match score indicative of a likelihood that the test sequencing data set associated with the nucleic acid molecule matches the reference sequence; and
(d) calling, using the one or more determined match scores, the presence or absence of the target short genetic variant in the test sample.

Embodiment 2. The method of embodiment 1, wherein obtaining comprises sequencing the test nucleic acid molecule using non-terminating nucleotides provided in separate nucleotide flows according to the flow-cycle order.

Embodiment 3. The method of embodiment 1 or embodiment 2, wherein the target short genetic variant is preselected prior to calling the presence or absence of the target short genetic variant in the test sample.

Embodiment 4. The method of embodiment 1 or embodiment 2, wherein the target short genetic variant is selected after calling the presence or absence of the target short genetic variant in the test sample based on a confidence of the call.

Embodiment 5. The method of any one of embodiments 1-4, comprising generating a personalized biomarker panel for a subject associated with the test sample, the biomarker panel comprising the target short genetic variant.

Embodiment 6. The method of any one of embodiments 1-5, comprising selecting the flow-cycle order.

Embodiment 7. The method of any one of embodiments 1-6, wherein the target sequencing data set is an expected target sequencing data set or the reference sequencing data set is an expected reference sequencing data set.

Embodiment 8. The method of embodiments 7, wherein the expected target sequencing data set and the expected reference sequencing data set are obtained by sequencing the target sequence and the reference sequence in silico.

Embodiment 9. The method of any one of embodiments 1-8, wherein the target sequencing data set differs from the reference sequencing data at more than two non-consecutive flow positions.

Embodiment 10. The method of any one of embodiments 1-9, wherein the target sequencing data set differs from the reference sequencing data at more than two consecutive flow positions.

Embodiment 11. The method of any one of embodiments 1-10, wherein the target sequence differs from the reference sequence at X base positions, and wherein the target sequencing data set differs from the reference sequencing data at (X+2) or more consecutive flow positions.

Embodiment 12. The method of embodiment 11, wherein the (X+2) flow position differences comprise differences between values substantially equal to zero and values substantially greater than zero.

Embodiment 13. The method of any one of embodiments 1-12, wherein the target sequencing data set differs from the reference sequencing data set across one or more flow-cycles.

Embodiment 14. The method of any one of embodiments 1-13, wherein the flow signals comprise a base count indicative of a number of bases of the test nucleic acid molecule sequenced at each flow position.

Embodiment 15. The method of any one of embodiments 1-14, wherein the flow signals comprises a statistical parameter indicative of a likelihood for at least one base count at each flow position, wherein the base count is indicative of a number of bases of the test nucleic acid molecule sequenced at the flow position.

Embodiment 16. The method of any one of embodiments 1-15, wherein the flow signals comprises a statistical parameter indicative of a likelihood for a plurality of base counts at each flow position, wherein each base count is indicative of a number of bases of the test nucleic acid molecule sequenced at the flow position.

Embodiment 17. The method of embodiment 16, wherein step (c) comprises:
  selecting the statistical parameter at each flow position in the test sequencing data set that corresponds with a base count of the target sequence at that flow position, and determining the match score indicative of the likelihood that the test sequencing data set matches the target sequence; or
  selecting the statistical parameter at each flow position in the test sequencing data set that corresponds with a base count of the reference sequence at that flow position, and determining the match score indicative of the likelihood that the test sequencing data set matches the reference sequence.

Embodiment 18. The method of embodiment 17, wherein the match score determined in step (c) is a combined value of the selected statistical parameters across the flow positions in the test sequencing data set.

Embodiment 19. The method of any one of embodiments 1-18, wherein step (c) comprises determining the match score indicative of the likelihood that the test sequencing data set matches the target sequence.

Embodiment 20. The method of any one of embodiments 1-19, wherein step (c) comprises determining the match score indicative of the likelihood that the test sequencing data set matches the reference sequence.

Embodiment 21. The method of any one of embodiments 1-20, wherein the one or more test sequencing data sets comprises a plurality of test sequencing data sets.

Embodiment 22. The method of embodiment 21, wherein the presence or absence of the target short genetic variant is separately called for each of the one or more test sequencing data sets.

Embodiment 23. The method embodiment 21 or 22, wherein at least a portion of the plurality of test sequencing data sets are associated with different test nucleic acid molecules have different sequencing start positions.

Embodiment 24. The method of any one of embodiments 1-23, wherein the flow-cycle order comprises 4 separate flows repeated in the same order.

Embodiment 25. The method of any one of embodiments 1-24, wherein the flow-cycle order comprises 5 or more separate flows.

Embodiment 26. The method of any one of embodiments 1-25, wherein the method is a computer-implemented method, comprising:
  selecting the target short genetic variant using one or more processors;
  obtaining the one or more test sequencing data sets by receiving, at the one or more processors, the one or more test sequencing data sets;
  determining the one or more match scores using the one or more processors; and
  calling the presence or absence of the target short genetic variant in the test sample using the one or more processors.

Embodiment 27. A system, comprising:
  one or more processors; and
  a non-transitory computer-readable medium that stores one or more programs comprising instructions for implementing the method of any one of embodiments 1-26.

Embodiment 28. A method for detecting a short genetic variant in a test sample, comprising:
  (a) obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate nucleotide flows according to a first flow-cycle order, and wherein the one or more first test sequencing data sets comprise flow signals at flow positions corresponding to the nucleotide flows;
  (b) obtaining one or more second test sequencing data sets, each second test sequencing data set associated with the same test nucleic acid molecule as a first test sequencing data set, wherein the second test sequencing data sets were determined by sequencing the one or more test nucleic acid molecules using non-terminating nucleotides provided in separate nucleotide flows according to a second flow-cycle order, wherein the first flow-cycle order and the second flow-cycle order are different, and wherein the test sequencing data set comprises flow signals at flow positions corresponding to the nucleotide flows;
  (c) determining, for each first sequencing data set and second sequencing data set, a match score for one or more candidate sequences, wherein the match score is indicative of a likelihood that the first test sequencing data set, the second test sequencing data set, or both, matches a candidate sequence from the one or more candidate sequences; and
  (d) calling, using the determined match scores, the presence or absence of a short genetic variant in the test sample.

Embodiment 29. The method of embodiment 28, comprising sequencing the test nucleic acid molecules using non-terminating nucleotides provided in separate nucleotide flows according to the first flow-cycle order, and sequencing the test nucleic acid molecules using non-terminating nucleotides provided in separate nucleotide flows according to the second flow-cycle order.

Embodiment 30. The method of embodiment 28 or 29, wherein the match score is indicative of a likelihood that the first test sequencing data set matches the candidate sequence, or the likelihood that the second test sequencing data set matches the candidate sequence.

Embodiment 31. The method of embodiment 28 or 29, wherein the match score is indicative of a likelihood that both the first test sequencing data set and the second sequencing data set match the candidate sequence.

Embodiment 32. The method of any one of embodiments 28-31, wherein the one or more candidate sequences comprises two or more different candidate sequences, the method comprising, for each nucleic acid molecule associated with a first sequencing data set and a second sequencing data set:
  selecting a candidate sequence from the two or more different candidate sequences, wherein the selected candidate sequence has the highest likelihood match with the first test sequencing data set, the second test sequencing data set, or both; and
  calling, using the selected candidate sequence, the presence or absence of the short genetic variant in the test sample.

Embodiment 33. The method of embodiment 32, wherein at least one non-selected candidate sequence from the two or more different candidate sequences differs from the selected candidate sequence at two or more flow positions according to the first flow-cycle order or the second flow-cycle order.

Embodiment 34. The method of embodiment 32, wherein at least one non-selected candidate sequence from the two or more different candidate sequences differs from the selected candidate sequence at two or more flow positions according to both the first flow-cycle order and the second flow-cycle order.

Embodiment 35. The method of embodiment 32, wherein at least one non-selected candidate sequence from the two or more different candidate sequences differs from the selected candidate sequence at two or more non-consecutive flow positions according to the first flow-cycle order or the second flow-cycle order.

Embodiment 36. The method of embodiment 32, wherein at least one non-selected candidate sequence from the two or more different candidate sequences differs from the selected candidate sequence at two or more non-consecutive flow positions according to both the first flow-cycle order and the second flow-cycle order.

Embodiment 37. The method of embodiment 32, wherein at least one non-selected candidate sequence from the two or more different candidate sequences differs from the selected candidate sequence at two or more consecutive flow positions according to the first flow-cycle order or the second flow-cycle order.

Embodiment 38. The method of embodiment 32, wherein at least one non-selected candidate sequence from the two or more different candidate sequences differs from the selected candidate sequence at two or more consecutive flow positions according to both the first flow-cycle order and the second flow-cycle order.

Embodiment 39. The method of embodiment 32, wherein at least one non-selected candidate sequence from the two or more different candidate sequences differs from the selected candidate sequence at 3 or more flow positions according to the first flow-cycle order or the second flow-cycle order.

Embodiment 40. The method of embodiment 32, wherein at least one non-selected candidate sequence from the two or more different candidate sequences differs from the selected candidate sequence at 3 or more flow positions according to both the first flow-cycle order and the second flow-cycle order.

Embodiment 41. The method of embodiment 32, wherein at least one non-selected candidate sequence from the two or more different candidate sequences differs from the selected candidate sequence at X base positions, and wherein the test sequencing data set associated with the test nucleic acid molecule differs from at least one non-selected candidate sequence from the two or more different candidate sequences at (X+2) or more flow positions according to the first flow-cycle order or the second flow-cycle order.

Embodiment 42. The method of embodiment 32, wherein at least one non-selected candidate sequence from the two or more different candidate sequences differs from the selected candidate sequence at X base positions, and wherein the test sequencing data set associated with the test nucleic acid molecule differs from at least one non-selected candidate sequence from the two or more different candidate sequences at (X+2) or more flow positions according to both the first flow-cycle order and the second flow-cycle order.

Embodiment 43. The method of embodiment 41 or 42, wherein the (X+2) flow position differences comprise differences between values substantially equal to zero and values substantially greater than zero.

Embodiment 44. The method of embodiment 32, wherein at least one non-selected candidate sequence from the two or more different candidate sequences differs from the selected candidate sequence across one or more flow-cycles according to the first flow-cycle order or the second flow-cycle order.

Embodiment 45. The method of embodiment 32, wherein at least one non-selected candidate sequence from the two or more different candidate sequences differs from the selected candidate sequence across one or more flow-cycles according to both the first flow-cycle order and the second flow-cycle order.

Embodiment 46. The method of any one of embodiments 28-45, wherein the flow signals comprise a base count indicative of a number of bases of the test nucleic acid molecule sequenced at each flow position.

Embodiment 47. The method of any one of embodiments 28-46, wherein the flow signals comprises a statistical parameter indicative of a likelihood for at least one base count at each flow position, wherein the base count is indicative of a number of bases of the test nucleic acid molecule sequenced at the flow position.

Embodiment 48. The method of any one of embodiments 28-47, wherein the flow signals comprises a statistical parameter indicative of a likelihood for a plurality of base counts at each flow position, wherein each base count is indicative of a number of bases of the test nucleic acid molecule sequenced at the flow position.

Embodiment 49. The method of embodiment 48, wherein determining the match score comprises, for each of the one or more different candidate sequences, selecting the statistical parameter at each flow position in the first test sequencing data set and the second test sequencing data set that corresponds with a base count of the candidate sequence at that flow position.

Embodiment 50. The method of embodiment 49, comprising, for the one or more different candidate sequences, generating a candidate sequencing data set comprising the base count of the candidate sequence at each flow position.

Embodiment 51. The method of embodiment 50, wherein the candidate sequencing data set is generated in silico.

Embodiment 52. The method of any one of embodiments 49-51, wherein the match score is a combined value of the selected statistical parameters across the flow positions in the first test sequencing data set and the second test sequencing data set.

Embodiment 53. The method of any one of embodiments 28-52, wherein at least a portion of the test nucleic acid molecules have different sequencing start positions.

Embodiment 54. The method of any one of embodiments 28-52, comprising:
selecting a target short genetic variant, wherein a target sequencing data set associated with a target sequence comprising the target short genetic variant differs from a reference sequencing data set associated with a reference sequence at two or more flow positions when the target sequencing data set and the reference sequencing data set are obtained by sequencing the target sequence using non-terminating nucleotides provided in separate nucleotide flows according to the first flow-cycle order or the second flow cycle order, wherein the first flow-cycle order is different from the second flow cycle order, and wherein the flow positions corresponds to the nucleotide flows;
wherein the one or more candidate sequences comprises the target sequence and the reference sequence.

Embodiment 55. The method of embodiment 54, wherein the target short genetic variant is pre-selected prior to calling the presence or absence of the target short genetic variant in the test sample.

Embodiment 56. The method of embodiment 54, wherein the target short genetic variant is selected after calling the presence or absence of the target short genetic variant in the test sample based on a confidence of the call.

Embodiment 57. The method of embodiment 56, comprising generating a personalized biomarker panel for a subject associated with the test sample, the biomarker panel comprising the target short genetic variant present in the test sample.

Embodiment 58. The method of any one of embodiments 54-57, wherein the reference sequencing data set is obtained by determining an expected reference sequencing data set if the reference sequence was sequenced using non-terminating nucleotides provided in separate flows according to the first flow-cycle order or the second flow-cycle order.

Embodiment 59. The method of any one of embodiments 54-57, wherein the reference sequencing data set is obtained by determining an expected reference sequencing data set if the reference sequence was sequenced using non-terminating nucleotides provided in separate flows according to both the first flow-cycle order and the second flow-cycle order.

Embodiment 60. The method of any one of embodiments 54-57, wherein the target sequence differs from the reference sequence at two or more flow positions according to both the first flow-cycle order and the second flow-cycle order.

Embodiment 61. The method of any one of embodiments 54-57, wherein the target sequence differs from the reference sequence at two or more non-consecutive flow positions according to the first flow-cycle order or the second flow-cycle order.

Embodiment 62. The method of any one of embodiments 54-57, wherein the target sequence differs from the reference sequence at two or more non-consecutive flow positions according to both the first flow-cycle order and the second flow-cycle order.

Embodiment 63. The method of any one of embodiments 54-57, wherein the target sequence differs from the reference sequence at two or more consecutive flow positions according to the first flow-cycle order or the second flow-cycle order.

Embodiment 64. The method of any one of embodiments 54-57, wherein the target sequence differs from the reference sequence at two or more consecutive flow positions according to both the first flow-cycle order and the second flow-cycle order.

Embodiment 65. The method of any one of embodiments 54-57, wherein the target sequence differs from the reference sequence at three or more flow positions according to the first flow-cycle order or the second flow-cycle order.

Embodiment 66. The method of any one of embodiments 54-57, wherein the target sequence differs from the reference sequence at three or more flow positions according to both the first flow-cycle order and the second flow-cycle order.

Embodiment 67. The method of any one of embodiments 54-57, wherein the target sequence differs from the reference sequence across one or more flow-cycles according to the first flow-cycle order or the second flow-cycle order.

Embodiment 68. The method of any one of embodiments 54-57, wherein the target sequence differs from the reference sequence across one or more flow-cycles according to both the first flow-cycle order and the second flow-cycle order.

Embodiment 69. The method of any one of embodiments 28-68, wherein the first flow-cycle order or the second flow-cycle order comprises 4 separate flows repeated in the same order.

Embodiment 70. The method of any one of embodiments 28-68, wherein the first flow-cycle order or the second flow-cycle order comprises 5 or more separate flows repeated in the same order.

Embodiment 71. The method of any one of embodiments 28-70, comprising:
sequencing the test nucleic acid molecule, comprising providing the non-terminating nucleotides in separate nucleotide flows according to the first flow-cycle order, extending a sequencing primer, and detecting the presence or absence of nucleotide incorporation into the sequencing primer after each nucleotide flow to generate the first test sequencing data set;
removing the extended sequencing primer; and
sequencing the same test nucleic acid molecule, comprising providing the non-terminating nucleotides in separate nucleotide flows according to the second flow-cycle order, extending a sequencing primer, and detecting the presence or absence of nucleotide incorporation into the sequencing primer after each nucleotide flow to generate the second test sequencing data set.

Embodiment 72. The method of any one of embodiments 28-71, wherein the method is a computer-implemented method, comprising:
receiving the one or more first sequencing data sets at one or more processors;
receiving the one or more first sequencing data sets at the one or more processors;
determining the match scores using the one or more processors; and
calling the presence or absence of the target short genetic variant in the test sample using the one or more processors.

Embodiment 73. A system, comprising:
one or more processors; and
a non-transitory computer-readable medium that stores one or more programs comprising instructions for implementing the method of any one of embodiments 28-72.

Embodiment 74. The method or system of any one of embodiments 1-73, wherein the separate flows comprise a single base type.

Embodiment 75. The method or system of any one of embodiments 1-74, wherein at least one of the separate flows comprise 2 or 3 different base types.

Embodiment 76. The method or system of any one of embodiments 1-75, comprising generating or updating a variant call file that indicates the presence, identity or absence of the short genetic variant in the test sample.

Embodiment 77. The method or system of any one of embodiments 1-76, comprising generating a report that indicates the presence, identity, or absence of the short genetic variant in the test sample.

Embodiment 78. The method or system of embodiment 77, wherein the report comprises a textual, probabilistic, numerical, or graphical output indicating the presence, identity, or absence of the short genetic variant in the test sample.

Embodiment 79. The method or system of embodiment 77 or 78, comprising providing the report to a patient or a healthcare representative of the patient.

Embodiment 78. The method or system of any one of embodiments 1-77, wherein the short genetic variant comprises a single nucleotide polymorphism.

Embodiment 79. The method or system of any one of embodiments 1-77, wherein the short genetic variant comprises an indel.

Embodiment 80. The method or system of any one of embodiments 1-79, wherein the test sample comprises fragmented DNA.

Embodiment 81. The method or system of any one of embodiments 1-80, wherein the test sample comprises cell-free DNA.

Embodiment 82. The method or system of embodiment 81, wherein the cell-free DNA comprises circulating tumor DNA (ctDNA).

Embodiment 83. A method of sequencing a nucleic acid molecule, comprising:
hybridizing the nucleic acid molecule to a primer to form a hybridized template;
extending the primer using labeled, non-terminating nucleotides provided in separate nucleotide flows according to a repeated flow-cycle order comprising five or more separate nucleotide flows; and
detecting a signal from an incorporated labeled nucleotide or an absence of a signal as the primer is extended by the nucleotide flows.

Embodiment 84. The method of embodiment 83, comprising detecting the signal or absence of the signal after each nucleotide flow.

Embodiment 85. The method of embodiment 83 or 84, comprising sequencing a plurality of nucleic acid molecules.

Embodiment 86. The method of embodiment 85, wherein the nucleic acid molecules in the plurality have different sequencing start positions with respect to a locus.

Embodiment 87. The method of any one of embodiments 83-86, wherein the test sample is cell-free DNA.

Embodiment 88. The method of any one of embodiments 83-86, wherein the cell-free DNA comprises circulating tumor DNA (ctDNA).

Embodiment 89. The method of any one of embodiments 83-86, wherein the flow-cycle order induces a signal change at more than two flow positions for 50% or more of possible SNP permutations at 5% or more of random sequencing start positions.

Embodiment 90. The method of any one of embodiments 83-86, wherein the flow-cycle order has an efficiency of 0.6 or more base incorporations per flow.

EXAMPLES

The application may be better understood by reference to the following non-limiting examples, which is provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1—SNP Detection

Figure 1C:
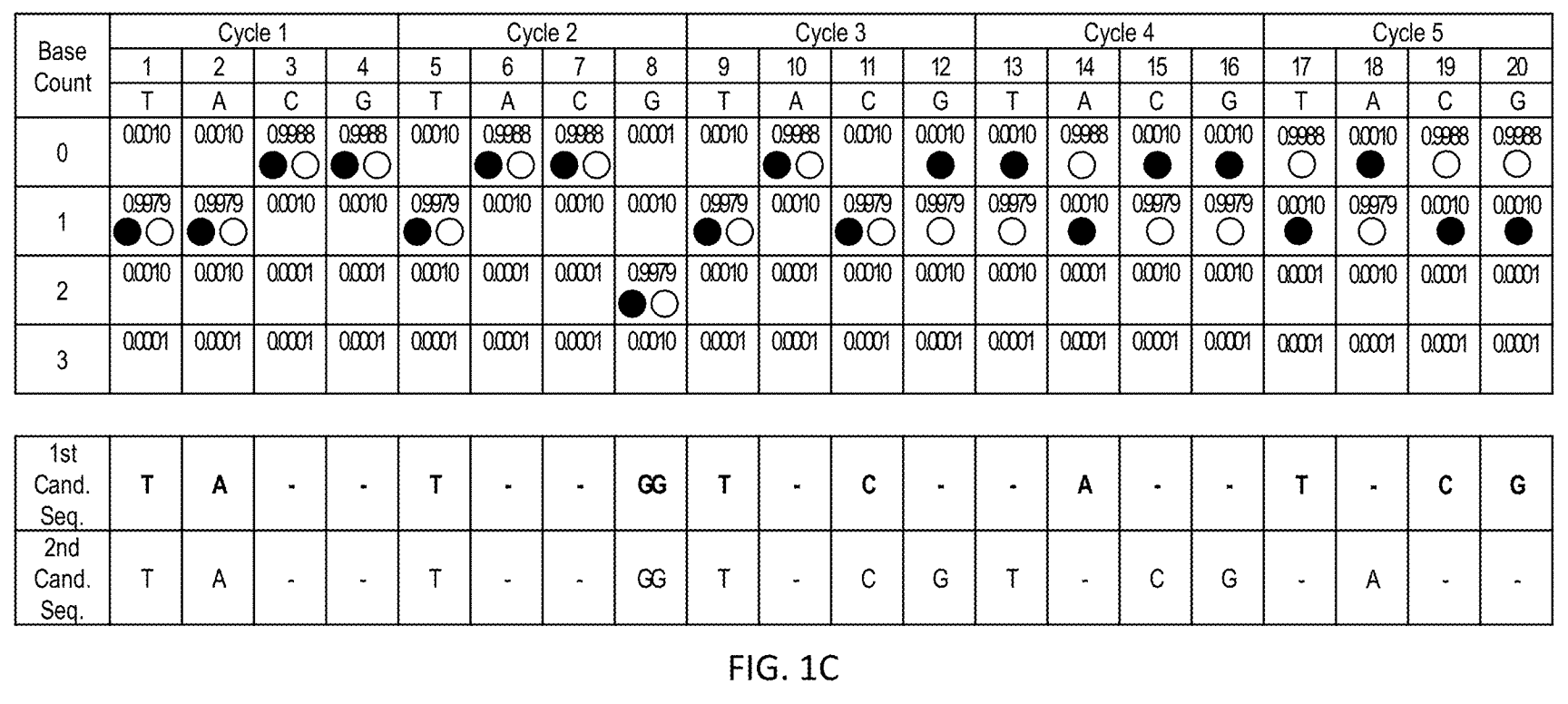

A hypothetical nucleic acid molecule is sequenced using non-terminating nucleotides provided in separate nucleotide flows according to a flow-cycle order A-T-G-C, resulting in the test sequencing data set shown in FIG. 1A. Each value of in the sequencing data set indicates the likelihood that the indicated base count at each flow position is correct. Based on the sequencing data set, a preliminary sequence is determined as TATGGTCGTCGA (SEQ ID NO: 1), which is mapped to a locus of reference genome. The locus of the reference genome is associated with potential haplotype sequences TATGGTCGTCGA (SEQ ID NO: 1) (H1) and TATGGTCATCGA (SEQ ID NO: 2) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −0.015, and the log likelihood of the sequencing data set if H2 is the correct sequence is −27.008. Thus, the sequence of H1 is selected for this nucleic acid molecule.

Example 2—Indel Detection

A hypothetical nucleic acid molecule is sequenced using non-terminating nucleotides provided in separate nucleotide flows according to a flow-cycle order A-T-G-C, resulting in the test sequencing data set shown in FIG. 8. Each value of in the sequencing data set indicates the likelihood that the indicated base count at each flow position is correct. Based on the sequencing data set (i.e., by selecting the most likely base count at each flow position), a preliminary sequence is determined as TATGGTCGATCG (SEQ ID NO: 8), which is mapped to a locus of reference genome. The locus of the reference genome is associated with potential haplotype sequences TATGGTCG-TCGA (SEQ ID NO: 7) (H1) and TATGGTCGATCG (SEQ ID NO: 8) (H2). A likelihood value associated with the base count of the haplotype sequence for each flow position is selected, for each haplotype. The likelihood of the sequencing data set given each haplotype is determined by multiplying the likelihood value associated with the base count of the haplotype sequence for each flow position. The log likelihood of the sequencing data set if H1 is the correct sequence is −24.009, and the log likelihood of the sequencing data set if H2 is the correct sequence is −0.015. Thus, the sequence of H2 is selected for this nucleic acid molecule.

Example 3—Extended Sequencing Flow Orders

Figure 9:
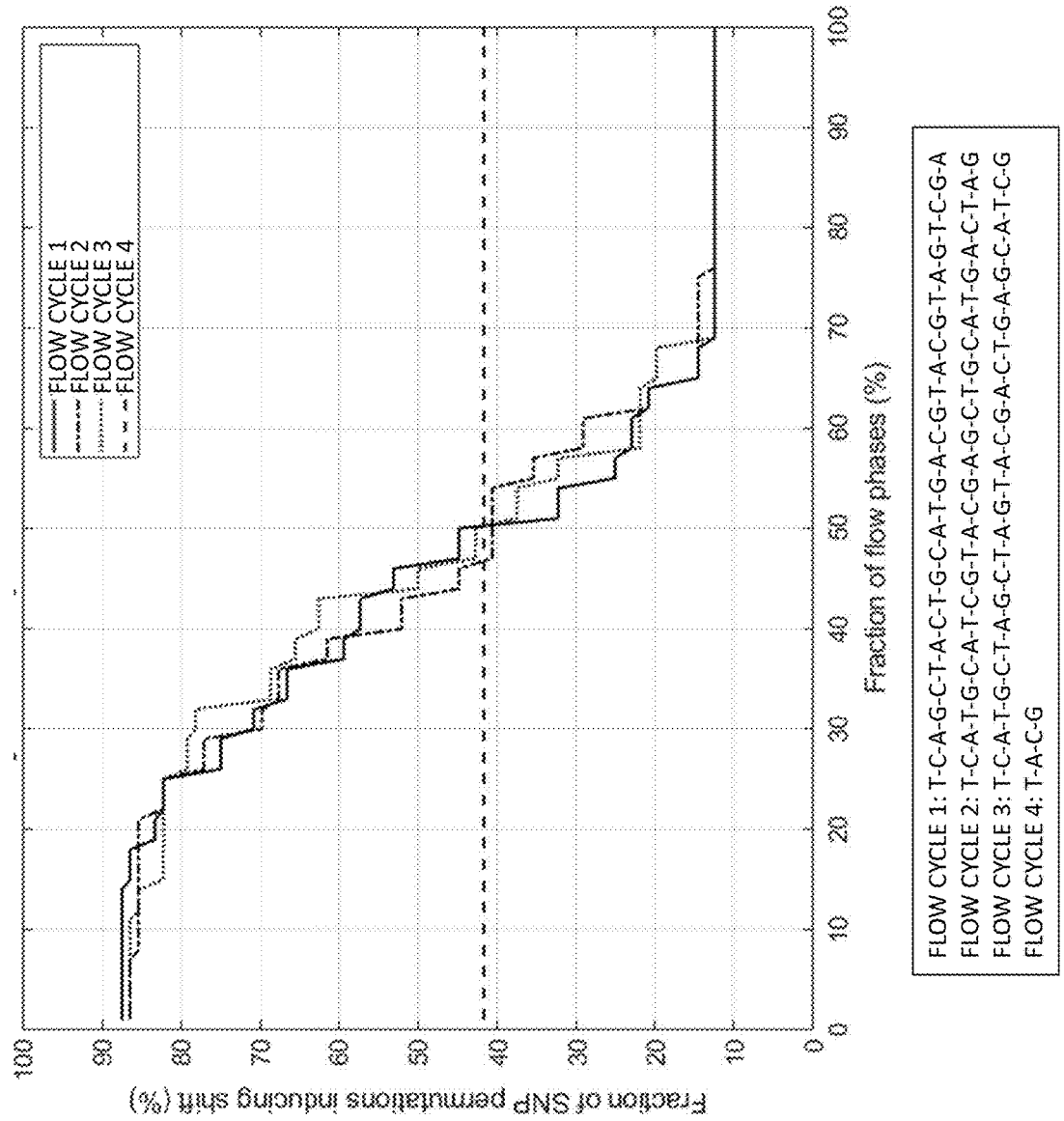
FIG. 9 shows, for four exemplary flow cycle orders (including 3 of which that are extended flow cycle orders), the sensitivity of detected a SNP permutation given random sequencing start positions.

More than a million extended sequencing flow orders were tested in silico for their likelihood to induce a signal change in more than two flow positions over the set of all possible SNPs (XYZ→XQZ where Q≠Y (and Q, X, Y, and Z are each any one of A, C, G, and T)). Extended flow orders were designed to have a minimum of 12 base sequences with all valid 2-base flow permutations, and flow orders having sequential base repeats were removed. All possible starting positions for the flow order were tested to assess sensitivity of the extended flow orders to induce the signal change at more than two flow positions. FIG. 9 and Table 2 show exemplary results of this analysis. In FIG. 9, the x-axis indicates the fraction of the flow phases (or fragmentation start positions), and the y-axis indicates the fraction of SNP permutations having induced a signal change at more than two flow positions. Several flow orders induce two or more signal differences at all possible (87.5%) SNP permutations for approximately 10% of reads (or flow start positions). A four base periodic flow only induces cycle shifts in only 42% of possible SNPs but it does this with all reads or flow phases. A final evaluation of efficiency was performed against a million base subset of human reference genome to establish viability. This is a practical measure of how efficiently the flow order extends the sequence given the patterns and biases in a real organism.

Example 4—SNP Detection Accuracy

The genome of DNA sample NA12878 (sample available from the Coriell Institute for Medical Research) was sequenced using non-terminating, fluorescently labeled nucleotides according to a four flow cycle (T-A-C-G). The sequencing run generated 415,900,002 reads with a mean length of 176 bases. 399,804,925 reads aligned (with BWA, version 0.7.17-r1188) to the hg38 reference genome.

After alignment, reads that perfectly aligned with the reference genome (178,634,625 reads) or reads that contained a single mismatch with the reference genome and aligned with a mapping quality score of 20 or more (27,265,661 reads) were selected. That is, 193,904,639 were excluded for further analysis, for example due to having an indel, multiple mismatches, or potentially incorrect (artefactual) alignment to the reference genome. The 27,265,661 reads were therefore presumed to include true positive NA12878 SNPs, as well as any false positive SNPs that arose from sequencing error. From this pool of 27,265,661 reads, sequencing reads that spanned a mismatched locus more than once were removed to reduce the effect of true positive NA12878 SNPs variants, resulting in a total of 3,413,700 reads containing a mismatch of depth 1).

The remaining 3,413,700 reads each included a mismatch that: (1) was expected to induce a cycle shift if the flowgram flow signal shifts by one full cycle (e.g., 4 flow positions) relative to the reference based on a flow cycle order, (2) potentially could induce cycle shift if a different flow cycle were used (e.g., it generates a new zero or a new non-zero signal in the flowgram), or (3) would not be able to induce a cycle shift regardless of the flow cycle order. Out of 3,413,700 mismatches 1,184,954 (34%) induced a cycle shift, while 1,546,588 (43%) could induce a cycle shift with a different flow order (i.e., "potential cycle shift"). In comparison, theoretical expectation of random mismatches would nominally suggest 42% cycle shift and 46% potential cycle shift mismatches. Overall, the rate of mismatches that induce a cycle shift was $3.7 \times 10^{-5}$ events/base, and the rate of mismatches that induce a potential cycle shift was $4.8 \times 10^{-5}$ events/base. Table 3 show the 10 most frequent single mismatches that induce a cycle shift and the relative percentages of incidence.

TABLE 3

| Reference | Read | % cases |
|---|---|---|
| TTT | TCT | 7.18 |
| AAA | AGA | 7.18 |
| GAG | GGG | 4.63 |
| CTC | CCC | 4.62 |
| CAG | CGG | 4.12 |
| CTG | CCG | 4.09 |
| AAC | AGC | 3.86 |
| GTT | GCT | 3.83 |
| CAT | CGT | 3.63 |
| GAT | GGT | 3.62 |

The performance of variant calling based on mismatches in each of the three different classes (i.e., induce cycle shift, potentially induce cycle shift, or do not and cannot induce cycle shift) was then evaluated. The reads were aligned to the reference genome with BWA and variant calling was performed using HaplotypeCaller tool of GATK (version 4). The resulting mismatch calls were filtered by discarding variant calls within a homopolymer longer than 10 bases, or within 10 bases adjacent to a homopolymer having a length 10 bases or more.

The mismatch calls were compared to calls generated for the same NA12878 by the genome-in-the bottle (GIAB) project to determined accuracy #TP/(#FP+#FN+#TP) for each class of mismatches. The sequencing data were randomly down sampled to the indicated mean genomic depth. Mismatches inducing cycle shifts and mismatches potentially inducing cycle shift had higher accuracy that mismatches not inducing cycle shifts, as demonstrated in Table 4.

TABLE 4

| Mismatch type | 30x | 22x | 15x | 8x |
|---|---|---|---|---|
| Cycle shift | 0.9834 | 0.981 | 0.981 | 0.9772 |
| No cycle shift | 0.9799 | 0.9759 | 0.9775 | 0.9696 |
| Potential cycle shift | 0.9826 | 0.9808 | 0.9795 | 0.9767 |

What is claimed is:

1. A method for detecting a short genetic variant associated with a disease in a test sample, comprising:
selecting a target short genetic variant associated with a disease, such that a target sequencing data set associated with a target sequence comprising the target short genetic variant differs from a reference sequencing data set associated with a reference sequence at four or more consecutive flow positions when the target sequencing data set and the reference sequencing data set are obtained by sequencing the target sequence and the reference sequence, respectively, using non-terminating nucleotides provided in separate flow positions according to a flow-cycle order;
obtaining one or more test sequencing data sets, each test sequencing data set associated with a test nucleic acid sequence, each test nucleic acid sequence at least partially overlapping a locus associated with the target short genetic variant and derived from the test sample, wherein the one or more test sequencing data sets were determined by sequencing the test sample using non-terminating nucleotides provided in separate flow positions according to the flow-cycle order;
determining, for each test nucleic acid sequence, a respective match score indicative of a likelihood that the test sequencing data set matches the target sequencing data set, or a respective match score indicative of a likelihood that the test sequencing data set matches the reference sequencing data set; and
calling, using the one or more respective match scores, the presence or absence of the target short genetic variant in the test sample;
wherein the target short genetic variant is selected prior to calling the presence or absence of the target short genetic variant in the test sample.

2. The method of claim 1, wherein the obtaining comprises sequencing test nucleic acid molecules derived from the test sample using non-terminating nucleotides provided in separate flow positions according to the flow-cycle order, and wherein each test nucleic acid molecule is associated with a respective test sequencing data set.

3. The method of claim 1, further comprising generating a personalized biomarker panel for a subject associated with the test sample, the personalized biomarker panel comprising the target short genetic variant.

4. The method of claim 1, further comprising selecting the flow-cycle order.

5. The method of claim 1, wherein the target sequencing data set and the reference sequencing data set are obtained by sequencing the target sequence and the reference sequence in silico.

6. The method of claim 2, wherein each of the one or more test sequencing data sets comprises flow signals at the separate flow positions, and the flow signals comprise a base count indicative of a number of bases of the respective test nucleic acid molecule sequenced at each flow position.

7. The method of claim 6, wherein the flow signals comprise a statistical parameter indicative of a likelihood for at least one base count at each flow position, wherein the base count is indicative of a number of bases of the respective test nucleic acid molecule sequenced at the flow position.

8. The method of claim 6, wherein the flow signals comprise a statistical parameter indicative of a likelihood for a plurality of base counts at each flow position, wherein each base count is indicative of a number of bases of the respective test nucleic acid molecule sequenced at the flow position.

9. The method of claim 8, wherein the determining comprises:
selecting the statistical parameter at each flow position in the test sequencing data set that corresponds with a base count of the target sequence at that flow position, and determining the respective match score indicative of the likelihood that the test sequencing data set matches the target sequencing data set; or
selecting the statistical parameter at each flow position in the test sequencing data set that corresponds with a base count of the reference sequence at that flow position, and determining the respective match score indicative of the likelihood that the test sequencing data set matches the reference sequencing data set.

10. The method of claim 9, wherein the respective match score determined in the determining is a combined value of the selected statistical parameters across the flow positions in the test sequencing data set.

11. The method of claim 1, wherein the determining comprises determining the respective match score indicative of the likelihood that the test sequencing data set matches the target sequencing data set.

12. The method of claim 1, wherein the determining comprises determining the respective match score indicative of the likelihood that the test sequencing data set matches the reference sequencing data set.

13. The method of claim 1, wherein the one or more test sequencing data sets comprises a plurality of test sequencing data sets.

14. The method of claim 13, wherein the presence or absence of the target short genetic variant is separately called for each of the one or more test sequencing data sets.

15. The method of claim 13, wherein at least a portion of the plurality of test sequencing data sets are associated with different test nucleic acid molecules have different sequencing start positions.

16. The method of claim 1, wherein the flow-cycle order comprises 4 separate flows repeated in the same order.

17. The method of claim 1, wherein the flow-cycle order comprises 5 or more separate flows.

18. A method for detecting a short genetic variant associated with a disease in a test sample, comprising:
  obtaining one or more first test sequencing data sets, each first test sequencing data set associated with a different test nucleic acid molecule derived from the test sample, wherein the first test sequencing data sets were determined by sequencing one or more test nucleic acid molecules using non-terminating nucleotides provided in separate flow positions according to a first flow-cycle order, and wherein the one or more first test sequencing data sets comprise flow signals at the separate flow positions;
  obtaining one or more second test sequencing data sets, each second test sequencing data set associated with a same respective test nucleic acid molecule as a corresponding first test sequencing data set, wherein the second test sequencing data sets were determined by re-sequencing the one or more test nucleic acid molecules using non-terminating nucleotides provided in separate flow positions according to a second flow-cycle order, wherein the first flow-cycle order and the second flow-cycle order are different, and wherein the one or more second test sequencing data sets comprises flow signals at the separate flow positions;
  determining, for each first sequencing data set and corresponding second sequencing data set, a respective match score to one or more candidate sequences, wherein the respective match score is indicative of a likelihood that the first test sequencing data set, the second test sequencing data set, or both, matches a candidate sequence from the one or more candidate sequences; and
  calling, using the determined match scores, the presence or absence of the short genetic variant in the test sample.

19. A method of sequencing a nucleic acid molecule, comprising:
  hybridizing the nucleic acid molecule to a primer to form a hybridized template;
  extending the primer using labeled, non-terminating nucleotides provided in separate flow positions according to a repeated flow-cycle order comprising five or more separate nucleotide flows; and
  detecting a signal from an incorporated labeled nucleotide or an absence of a signal as the primer is extended by the nucleotide flows.

* * * * *